US008628463B2

(12) United States Patent
Ogdahl et al.

(10) Patent No.: US 8,628,463 B2
(45) Date of Patent: Jan. 14, 2014

(54) ADJUSTABLE TENSION INCONTINENCE SLING ASSEMBLIES

(75) Inventors: Jason W. Ogdahl, Minnetonka, MN (US); Jessica L. Roll, Minnetonka, MN (US); Robert E. Lund, Minnetonka, MN (US); Kelly Ann Chapman, Minnetonka, MN (US); José W. Jimenez, Minnetonka, MN (US); Amanda J. Heys, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 482 days.

(21) Appl. No.: 12/308,598

(22) PCT Filed: Jun. 22, 2007

(86) PCT No.: PCT/US2007/014780
§ 371 (c)(1),
(2), (4) Date: Jul. 26, 2010

(87) PCT Pub. No.: WO2007/149593
PCT Pub. Date: Dec. 27, 2007

(65) Prior Publication Data
US 2011/0124954 A1 May 26, 2011

Related U.S. Application Data

(60) Provisional application No. 60/805,544, filed on Jun. 22, 2006, provisional application No. 60/806,664, filed on Jul. 6, 2006.

(51) Int. Cl.
*A61F 2/02* (2006.01)
*A61F 2/00* (2006.01)
(52) U.S. Cl.
USPC ............................................. 600/30; 600/29

(58) Field of Classification Search
USPC ....................................................... 600/30, 29
See application file for complete search history.

(56) References Cited

U.S. PATENT DOCUMENTS 3,384,073 A   5/1968   Van Winkle, Jr.
3,789,828 A   2/1974   Schulte
(Continued)

FOREIGN PATENT DOCUMENTS

AU   2002241673   11/2005
CA   2404459      8/2005
(Continued)

OTHER PUBLICATIONS

"Introducing: AlloSling Fascia The Natural Choice for Suburethral Sling Provedures", Advertisement from UroMed Corporation (1 page).

(Continued)

*Primary Examiner* — Christine Matthews
*Assistant Examiner* — Sunita Reddy
(74) *Attorney, Agent, or Firm* — Kagan Binder, PLLC

(57) ABSTRACT

Systems for providing support to body tissue to alleviate incontinence are disclosed that comprise an elongated incontinence sling (20) having a central support portion (40) adapted to be positioned to support any one of the urethra or anus (58, 67) and first and second sling end portions (42, 44) extending from the central support portion through body tissue and a tension adjustment mechanism acting on or within one or both of the sling end portions. The sling tension adjustment mechanism comprises one or more of a sling tensioning suture (312, 314) or band, and a tensioning device (310) coupled to a suture or band free end.

20 Claims, 19 Drawing Sheets

(56) References Cited

U.S. PATENT DOCUMENTS

| | | |
|---|---|---|
| 4,548,202 A | 10/1985 | Duncan |
| 4,632,100 A | 12/1986 | Somers et al. |
| 4,873,976 A | 10/1989 | Schreiber |
| 4,938,760 A | 7/1990 | Burton et al. |
| 4,969,892 A | 11/1990 | Burton et al. |
| 4,979,956 A | 12/1990 | Silvestrini |
| 5,013,292 A | 5/1991 | Lemay |
| 5,013,316 A | 5/1991 | Goble et al. |
| 5,019,032 A | 5/1991 | Robertson |
| 5,053,043 A | 10/1991 | Gottesman et al. |
| 5,085,661 A | 2/1992 | Moss |
| 5,112,344 A | 5/1992 | Petros |
| 5,141,520 A | 8/1992 | Goble et al. |
| 5,149,329 A | 9/1992 | Richardson |
| 5,188,636 A | 2/1993 | Fedotov |
| 5,203,864 A | 4/1993 | Phillips |
| 5,209,756 A | 5/1993 | Seedhom et al. |
| 5,256,133 A | 10/1993 | Spitz |
| 5,268,001 A | 12/1993 | Nicholson et al. |
| 5,269,783 A | 12/1993 | Sander |
| 5,328,077 A | 7/1994 | Lou |
| 5,337,736 A | 8/1994 | Reddy |
| 5,354,292 A | 10/1994 | Braeuer et al. |
| 5,362,294 A | 11/1994 | Seitzinger |
| 5,370,662 A | 12/1994 | Stone et al. |
| 5,376,097 A | 12/1994 | Phillips |
| 5,383,904 A | 1/1995 | Totakura et al. |
| 5,520,700 A | 5/1996 | Beyar et al. |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,584,860 A | 12/1996 | Goble et al. |
| 5,591,163 A | 1/1997 | Thompson |
| 5,591,206 A | 1/1997 | Moufarrege |
| 5,628,756 A | 5/1997 | Barker, Jr. et al. |
| 5,643,320 A | 7/1997 | Lower et al. |
| 5,647,836 A | 7/1997 | Blake et al. |
| 5,669,935 A | 9/1997 | Rosenman et al. |
| 5,674,247 A | 10/1997 | Sohn |
| 5,690,655 A | 11/1997 | Hart et al. |
| 5,697,931 A | 12/1997 | Thompson |
| 5,709,708 A | 1/1998 | Thal |
| 5,725,529 A | 3/1998 | Nicholson et al. |
| 5,725,541 A | 3/1998 | Anspach, III et al. |
| 5,741,282 A | 4/1998 | Anspach, III et al. |
| 5,782,862 A | 7/1998 | Bonuttie |
| 5,807,403 A | 9/1998 | Beyar et al. |
| 5,836,314 A | 11/1998 | Benderev et al. |
| 5,842,478 A | 12/1998 | Benderev et al. |
| 5,873,891 A | 2/1999 | Sohn |
| 5,899,909 A | 5/1999 | Claren et al. |
| 5,904,692 A | 5/1999 | Steckel et al. |
| 5,922,026 A | 7/1999 | Chin |
| 5,925,047 A | 7/1999 | Errico et al. |
| 5,934,283 A | 8/1999 | Willem et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,007,539 A | 12/1999 | Kirsch et al. |
| 6,010,447 A | 1/2000 | Kardjian |
| 6,019,768 A | 2/2000 | Wenstrom et al. |
| 6,027,523 A | 2/2000 | Schmieding |
| 6,036,701 A | 3/2000 | Rosenman |
| 6,039,686 A | 3/2000 | Kovac |
| 6,042,534 A | 3/2000 | Gellman et al. |
| 6,042,536 A | 3/2000 | Tihon et al. |
| 6,048,351 A | 4/2000 | Gordon et al. |
| 6,053,935 A | 4/2000 | Brenneman et al. |
| 6,056,688 A | 5/2000 | Benderev et al. |
| 6,068,591 A | 5/2000 | Bruckner et al. |
| 6,077,216 A | 6/2000 | Benderev et al. |
| 6,099,551 A | 8/2000 | gabby |
| 6,099,552 A | 8/2000 | Adams |
| 6,106,545 A | 8/2000 | Egan |
| 6,110,101 A | 8/2000 | Tihon et al. |
| 6,117,067 A | 9/2000 | Gil-Vernet |
| 6,127,597 A | 10/2000 | Beyar et al. |
| 6,168,611 B1 | 1/2001 | Risvi |
| 6,200,330 B1 | 3/2001 | Benderev et al. |
| 6,221,005 B1 | 4/2001 | Bruckner et al. |
| 6,241,736 B1 | 6/2001 | Sater et al. |
| 6,245,082 B1 | 6/2001 | Gellman et al. |
| 6,264,676 B1 | 7/2001 | Gellman et al. |
| 6,273,852 B1 | 8/2001 | Lehe et al. |
| 6,306,079 B1 | 10/2001 | Trabucco |
| 6,319,272 B1 | 11/2001 | Brenneman |
| 6,322,492 B1 | 11/2001 | Kovac |
| 6,328,686 B1 | 12/2001 | Kovac |
| 6,334,446 B1 | 1/2002 | Beyar |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,423,072 B1 | 7/2002 | Zappala |
| 6,423,080 B1 | 7/2002 | Gellman et al. |
| 6,440,154 B2 | 8/2002 | gellman et al. |
| 6,451,024 B1 | 9/2002 | Thompson et al. |
| 6,454,778 B2 | 9/2002 | Kortenbach |
| 6,475,139 B1 | 11/2002 | Miller |
| 6,478,727 B2 | 11/2002 | Scetbon |
| 6,491,703 B1 | 12/2002 | Ulmsten |
| 6,506,190 B1 | 1/2003 | Walshe |
| 6,544,273 B1 | 4/2003 | Harari et al. |
| 6,575,897 B1 | 6/2003 | Ory |
| 6,582,443 B2 | 6/2003 | Cabak et al. |
| 6,592,610 B2 | 7/2003 | Beyar |
| 6,599,235 B2 | 7/2003 | Kovac |
| 6,612,977 B2 | 9/2003 | Staskin |
| 6,635,058 B2 | 10/2003 | Beyar et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,685,629 B2 | 2/2004 | Therin |
| 6,702,827 B1 | 3/2004 | Lund |
| 6,730,110 B1 | 5/2004 | Harari et al. |
| 6,746,455 B2 | 6/2004 | Beyar et al. |
| 6,755,781 B2 | 6/2004 | Gellman |
| 6,881,184 B2 | 4/2005 | Zappala |
| 6,908,425 B2 | 6/2005 | Luscombe |
| 6,908,473 B2 | 6/2005 | Skiba et al. |
| 6,911,002 B2 | 6/2005 | Fierro |
| 6,953,428 B2 | 10/2005 | Gellman et al. |
| 6,960,160 B2 | 11/2005 | Browning |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,025,063 B2 | 4/2006 | Snitkin |
| 7,025,772 B2 | 4/2006 | Gellman et al. |
| 7,048,682 B2 | 5/2006 | Neisz et al. |
| 7,056,333 B2 | 6/2006 | Walshe |
| 7,070,558 B2 | 7/2006 | Gellman et al. |
| 7,083,568 B2 | 8/2006 | Neisz et al. |
| 7,087,065 B2 | 8/2006 | Ulmsten et al. |
| 7,112,171 B2 | 9/2006 | Rocheleau et al. |
| 7,112,210 B2 | 9/2006 | Ulmsten et al. |
| 7,121,997 B2 | 10/2006 | Kammerer et al. |
| 7,198,597 B2 | 4/2007 | Siegel et al. |
| 7,226,408 B2 | 6/2007 | Harai et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,267,645 B2 | 9/2007 | Anderson et al. |
| 7,291,104 B2 | 11/2007 | Neisz et al. |
| 7,297,102 B2 | 11/2007 | Smith et al. |
| 7,303,525 B2 | 12/2007 | Watschke et al. |

(56) References Cited

U.S. PATENT DOCUMENTS

| | | |
|---|---|---|
| 7,326,213 B2 | 2/2008 | Benderev et al. |
| 7,347,812 B2 | 3/2008 | Mellier |
| 7,351,196 B2 | 4/2008 | Goldmann et al. |
| 7,351,197 B2 | 4/2008 | Montpetit et al. |
| 7,364,541 B2 | 4/2008 | Chu et al. |
| 7,387,634 B2 | 6/2008 | Benderev |
| 7,402,133 B2 | 7/2008 | Chu et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,431,690 B2 | 10/2008 | Merade et al. |
| 7,494,495 B2 | 2/2009 | Delorme et al. |
| 7,513,865 B2 | 4/2009 | Bourne et al. |
| 7,527,588 B2 | 5/2009 | Zaddem et al. |
| 7,547,316 B2 | 6/2009 | Priewe et al. |
| 7,588,598 B2 | 9/2009 | Delorme et al. |
| 7,601,118 B2 | 10/2009 | Smith et al. |
| 7,621,865 B2 | 11/2009 | Gellman et al. |
| 7,637,860 B2 | 12/2009 | MacLean |
| 7,686,759 B2 | 3/2010 | Sater |
| 7,691,050 B2 | 4/2010 | Gellman et al. |
| 7,691,052 B2 | 4/2010 | Gellman et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,762,969 B2 | 7/2010 | Gellman et al. |
| 7,766,926 B2 | 8/2010 | Bosley et al. |
| 7,789,821 B2 | 9/2010 | Browning |
| 7,794,385 B2 | 9/2010 | Rosenblatt |
| 7,828,715 B2 | 11/2010 | Haverfield |
| 2001/0000533 A1 | 4/2001 | Kovac |
| 2001/0023356 A1 | 9/2001 | Raz |
| 2001/0027321 A1 | 10/2001 | Gellman et al. |
| 2001/0041895 A1 | 11/2001 | Beyar et al. |
| 2002/0007222 A1 | 1/2002 | Desai |
| 2002/0022841 A1 | 2/2002 | Kovac |
| 2002/0028980 A1 | 3/2002 | Thierfelder et al. |
| 2002/0035369 A1 | 3/2002 | Beyar et al. |
| 2002/0050277 A1 | 5/2002 | Beyer |
| 2002/0055748 A1 | 5/2002 | Gellman et al. |
| 2002/0058959 A1 | 5/2002 | Gellman et al. |
| 2002/0082619 A1 | 6/2002 | Cabak et al. |
| 2002/0091373 A1 | 7/2002 | Berger |
| 2002/0095064 A1 | 7/2002 | Beyar |
| 2002/0095163 A1 | 7/2002 | Beyar |
| 2002/0095181 A1 | 7/2002 | Beyar |
| 2002/0099260 A1 | 7/2002 | Suslian et al. |
| 2002/0128681 A1 | 9/2002 | Broome et al. |
| 2002/0138025 A1 | 9/2002 | Gellman et al. |
| 2002/0147382 A1 | 10/2002 | Neisz et al. |
| 2002/0151909 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz |
| 2003/0023137 A1 | 1/2003 | Gellman et al. |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |
| 2003/0065402 A1 | 4/2003 | Anderson et al. |
| 2003/0176875 A1 | 9/2003 | Anderson |
| 2004/0015048 A1* | 1/2004 | Neisz et al. ............ 600/37 |
| 2004/0015057 A1 | 1/2004 | Rocheleau et al. |
| 2004/0039453 A1 | 2/2004 | Anderson et al. |
| 2004/0073235 A1 | 4/2004 | Lund |
| 2004/0138747 A1* | 7/2004 | Kaladelfos ............ 623/13.13 |
| 2004/0193215 A1 | 9/2004 | Harari et al. |
| 2004/0225181 A1 | 11/2004 | Chu et al. |
| 2004/0267088 A1 | 12/2004 | Kammerer |
| 2005/0004576 A1 | 1/2005 | Benderev |
| 2005/0038451 A1 | 2/2005 | Rao et al. |
| 2005/0090827 A1* | 4/2005 | Gedebou ............ 606/72 |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0058574 A1* | 3/2006 | Priewe et al. ............ 600/29 |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac |
| 2006/0173237 A1 | 8/2006 | Jacquetin |
| 2006/0195007 A1 | 8/2006 | Anderson |
| 2006/0195011 A1 | 8/2006 | Arnal |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0260618 A1 | 11/2006 | Hodroff et al. |
| 2006/0287571 A1 | 12/2006 | Gozzi |
| 2007/0015953 A1 | 1/2007 | MacLean |
| 2007/0078295 A1 | 4/2007 | landgrebe |
| 2007/0173864 A1 | 7/2007 | Chu |
| 2008/0039678 A1 | 2/2008 | Montpetit et al. |
| 2009/0005634 A1 | 1/2009 | Rane |
| 2009/0012353 A1 | 1/2009 | Beyer |
| 2009/0221867 A1 | 9/2009 | Ogdahl et al. |
| 2009/0221868 A1 | 9/2009 | Evans |
| 2009/0240102 A1 | 9/2009 | Rane et al. |
| 2009/0259092 A1 | 10/2009 | Ogdahl et al. |
| 2010/0010631 A1 | 1/2010 | Otte et al. |
| 2010/0094079 A1 | 4/2010 | Inman |
| 2010/0152528 A1 | 6/2010 | Chapmenan et al. |
| 2010/0168505 A1 | 7/2010 | Inman et al. |
| 2010/0174134 A1 | 7/2010 | Anderson et al. |
| 2010/0261950 A1 | 10/2010 | Lund et al. |
| 2010/0261952 A1 | 10/2010 | Montpetit et al. |

FOREIGN PATENT DOCUMENTS

| | | |
|---|---|---|
| DE | 19544162 | 4/1997 |
| DE | 20016866 | 3/2007 |
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 1342450 B1 | 9/2003 |
| FR | 2787990 A1 | 7/2000 |
| FR | 2852817 | 10/2004 |
| IT | 1299162 | 4/1998 |
| WO | WO9310715 A1 | 6/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937216 A1 | 7/1999 |
| WO | WO9937217 A1 | 7/1999 |
| WO | WO9952450 A1 | 10/1999 |
| WO | WO9953844 A1 | 10/1999 |
| WO | WO9958074 A1 | 11/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |

(56) References Cited

FOREIGN PATENT DOCUMENTS

| | | |
|---|---|---|
| WO | WO0030556 A1 | 6/2000 |
| WO | WO0040158 A2 | 7/2000 |
| WO | WO0057796 A1 | 10/2000 |
| WO | WO0057812 A1 | 10/2000 |
| WO | WO0066030 A1 | 11/2000 |
| WO | WO0074594 A1 | 12/2000 |
| WO | WO0074613 A1 | 12/2000 |
| WO | WO0074633 A2 | 12/2000 |
| WO | WO0139670 A1 | 6/2001 |
| WO | WO0145588 A1 | 6/2001 |
| WO | WO0145589 A1 | 6/2001 |
| WO | WO0228312 A1 | 4/2002 |
| WO | WO0228315 A2 | 4/2002 |
| WO | WO0230293 A1 | 4/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 A1 | 9/2002 |
| WO | WO02071953 A2 | 9/2002 |
| WO | WO02078552 A1 | 10/2002 |
| WO | WO03013392 A2 | 2/2003 |
| WO | WO03003778 A1 | 4/2003 |
| WO | WO03034939 A1 | 5/2003 |
| WO | WO03068107 A1 | 8/2003 |
| WO | WO03073960 A1 | 9/2003 |
| WO | WO03075792 A1 | 9/2003 |
| WO | WO03086205 A2 | 10/2003 |
| WO | WO03092546 A2 | 11/2003 |
| WO | WO03096928 A1 | 11/2003 |
| WO | WO03096929 A1 | 11/2003 |
| WO | WO2004012626 A1 | 2/2004 |
| WO | WO2004016196 A2 | 2/2004 |
| WO | WO2004017862 A2 | 3/2004 |
| WO | WO2004045457 A1 | 6/2004 |
| WO | WO2005004727 A1 | 1/2005 |
| WO | WO2005037132 A2 | 4/2005 |
| WO | WO2005046511 A2 | 5/2005 |
| WO | WO2005048850 A2 | 6/2005 |
| WO | WO2005079702 A1 | 9/2005 |
| WO | WO2005094741 A1 | 10/2005 |
| WO | WO2005112842 A1 | 12/2005 |
| WO | WO2005122954 A1 | 12/2005 |
| WO | WO2006007190 A1 | 1/2006 |
| WO | WO2006015031 A2 | 2/2006 |
| WO | WO2006031879 A1 | 3/2006 |
| WO | WO2006069078 | 6/2006 |
| WO | WO2006108145 A1 | 10/2006 |
| WO | WO2006002012 A1 | 1/2007 |
| WO | WO2007002071 A1 | 1/2007 |
| WO | WO2007011341 A1 | 1/2007 |
| WO | WO2007014241 A1 | 2/2007 |
| WO | WO2007016083 A1 | 2/2007 |
| WO | WO2007016698 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |

OTHER PUBLICATIONS

Advantage A/T™, Surgical Mesh Sling Kit, Boston Scientific, 6 pages (2002).
Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).
AlloSource product literature (11pages).
Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).
Benderev, Theodore V., MD, A Modified Percutaneous Outpatient Bladder Neck Suspension System, Journal of Urology, vol. 152, pp. 2316-2320 (Dec. 1994).
Benderev, Theodore V., MD, Anchor Fixation and Other Modifications of Endoscopic Bladder Neck Suspension, Urology, vol. 40, No. 5, pp. 409-418 (Nov. 1992).
Blaivas, Jerry et al., Pubovaginal Fascial Sling for the Treatment of Complicated Stress Urinary Incontinence, The Journal of Urology, vol. 145, pp. 1214-1218 (Jun. 1991).
Blaivas, Jerry et al., Type III Stress Urinary Incontinence: Importance of Proper Diagnosis and Treatment, Surgical Forum, pp. 473-475, (1984).
Blavis, Jerry, Commentary: Pubovaginal Sling Procedure, Experience with Pubovaginal Slings, pp. 93-101 (1990).
Bryans, Fred E., Marlex Gauze Hammock Sling Operation With Cooper's Ligament Attachment in the Management of Recurrent Urinary Stress Incontinence, American Journal of Obstetrics and Gynecology, vol. 133, pp. 292-294 (Feb. 1979).
Capio™ CL—Transvaginal Suture Capturing Device—Transvaginal Suture Fixation to Cooper's Ligament for Sling Procedures, Boston Scientific, Microvasive®, 8 pages, (2002).
Choe, Jong M. et al., GORE-TEX Patch Sling: 7 Years Later, Urology, vol. 54, pp. 641-646 (1999).
Dargent, D. et al., Insertion of a Suburethral Sling Through the Obturator Membrane in the Treatment of Female Urinary Incontinence, Gynecol Obstet Fertil, vol. 30, pp. 576-582 (2002).
Decter, Ross M., Use of the Fascial Sling for Neurogenic Incontinence: Lessons Earned, The Journal of Urology, vol. 150, pp. 683-686 (Aug. 1993).
Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.
Falconer. C. et al., Influence of Different Sling Materials of Connective Tissue Metabolism in Stress Urinary Incontinent Women, International Urogynecology Journal, Supp. 2, pp. S19-S23 (2001).
Gynecare TVT Tension-Free Support for Incontinence. The tension-free solution to female Incontinence, Gynecare Worldwide,6 pages, (2002).
Handa, Victoria L. et al, Banked Human Fascia Lata for the Suburethral Sling Procedure: A Preliminary Report, Obstetrics & Gynecology, vol. 88 No. 6, 5 pages (Dec. 1996).
Kersey, J., The Gauze Hammock Sling Operation of the Treatment of Stress Incontintence, British Journal of Obstetrics and Gynaecology, vol. 90, pp. 945-949 (Oct. 1983).
Klutke, John M.D. et al, The promise of tension-free vaginal tape for female SUI, Contemporary Urology, 7 pages (Oct. 2000).
Korda, A. et al., Experience With Silastic Slings for Female Urinary Incontience, Aust NZ J. Obstet Gynaecol, vol. 29, pp. 150-154 (May 1989).
Kovac, S. Robert, et al, Pubic Bone Suburethral Stabilization Sling: A Long Term Cure for SUI?, Contemporary OB/GYN, 10 pages (Feb. 1998).
Morgan, J. E., A Sling Operation, Using Marlex Polypropylene Mesh, for the Treatment of Recurrent Stress Incontinence, Am. J. Obst. & Gynecol, pp. 369-377 (Feb. 1970).
Nichols, David H., The Mersilene Mesh Gauze-Hammock for Severe Urinary Stress Incontinence, Obstetrics and Gynecology, vol. 41, pp. 88-93 (Jan. 1973).
Niknejad, Kathleen et al., Autologous and Synthetic Urethral Slings for Female Incontinence, Urol Clin N Am, vol. 29, pp. 597-611 (2002).
Norris, Jeffrey P. et al., Use of Synthetic Material in Sling Surgery: A Minimally Invasive Approach, Journal of Endourology, vol. 10, pp. 227-230 (Jun. 1996).
O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).

(56) References Cited

OTHER PUBLICATIONS

Ostergard, Donald R. et al., Urogynecology and Urodynamics Theory and Practice, pp. 569-579 (1996).

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45-50 (1999).

Ridley, John H., Appraisal of the Goebell-Frangenheim-Stoeckel Sling Procedure, American Journal Obst & Gynec., vol. 95, No. 5, pp. 741-721 (Jul. 1, 1986).

SABRE™ Bioabsorbable Sling, Generation Now, Mentor, 4 pages (May 2002).

SABRE™ Surgical Procedure, Mentor, 6 pages (Aug. 2002).

Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).

Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 441-415 (Mar. 1987).

Stamey, Thomas A., M.D., Endoscopic Suspension of the Vesical Neck for Urinary Incontinence in Females, Ann. Surgery, vol. 192 No. 4, pp. 465-471 (Oct. 1980).

Stanton, Stuart L., Suprapubic Approaches for Stress Incontinence in Women, Journal of American Geriatrics Society, vol. 38, No. 3, pp. 348-351 (Mar. 1990).

Stanton, Stuart, Springer-Veglag, Surgery of Female Incontinence, pp. 105-113 (1986).

Studdiford, William E., Transplantation of Abdominal Fascia for the Relief of Urinary Stress Incontinence, American Journal of Obstetrics and Gynecology, pp. 764-775 (1944).

TVT Tension-free Vaginal Tape, Gynecare, Ethicon, Inc., 6 pages (1999).

Ulmsten, U. et al., An Ambulatory Surgical Procedure Under Local Anesthesia for Treatment of Female Urinary Incontinence, International Urogynecology Journal, vol. 7. pp. 81-86 (May 1996).

Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).

Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).

Vesica® Percutaneous Bladder Neck Stabilization Kit, A New Approach to Bladder Neck Suspenison, Microvasive® Boston Scientific Corporation, 4 pages (1995).

Vesica® Sling Kits, Simplifying Sling Procedures, Microvasive® Boston Scientific Corporation, 4 pages (1998).

Walters, Mark D., Percutaneous Suburethral Slings: State of the Art, Presented at the conference of the American Urogynecologic Society, Chicago, 29 pages (Oct. 2001).

Drutz, H.P. et al., Clinical and Urodynamic Re-Evaluation of Combined Abdominovaginal Marlex Sling Operations for Recurrent Stress Urinary Incontinence, International Urogynecology Journal, vol. 1, pp. 70-73 (1990).

Precision Twist, Low Profile design for Precise Anchor Placement, Boston Scientific Microvasive, 2001 2 pp.

Vesica Sling Kit, Microvasive Boston Scientific, 1997, 6pp.

Precision Tack, The Precise Approach to Transvaginal Sling Procedures, Boston Scientific, 1998, 4pp.

* cited by examiner

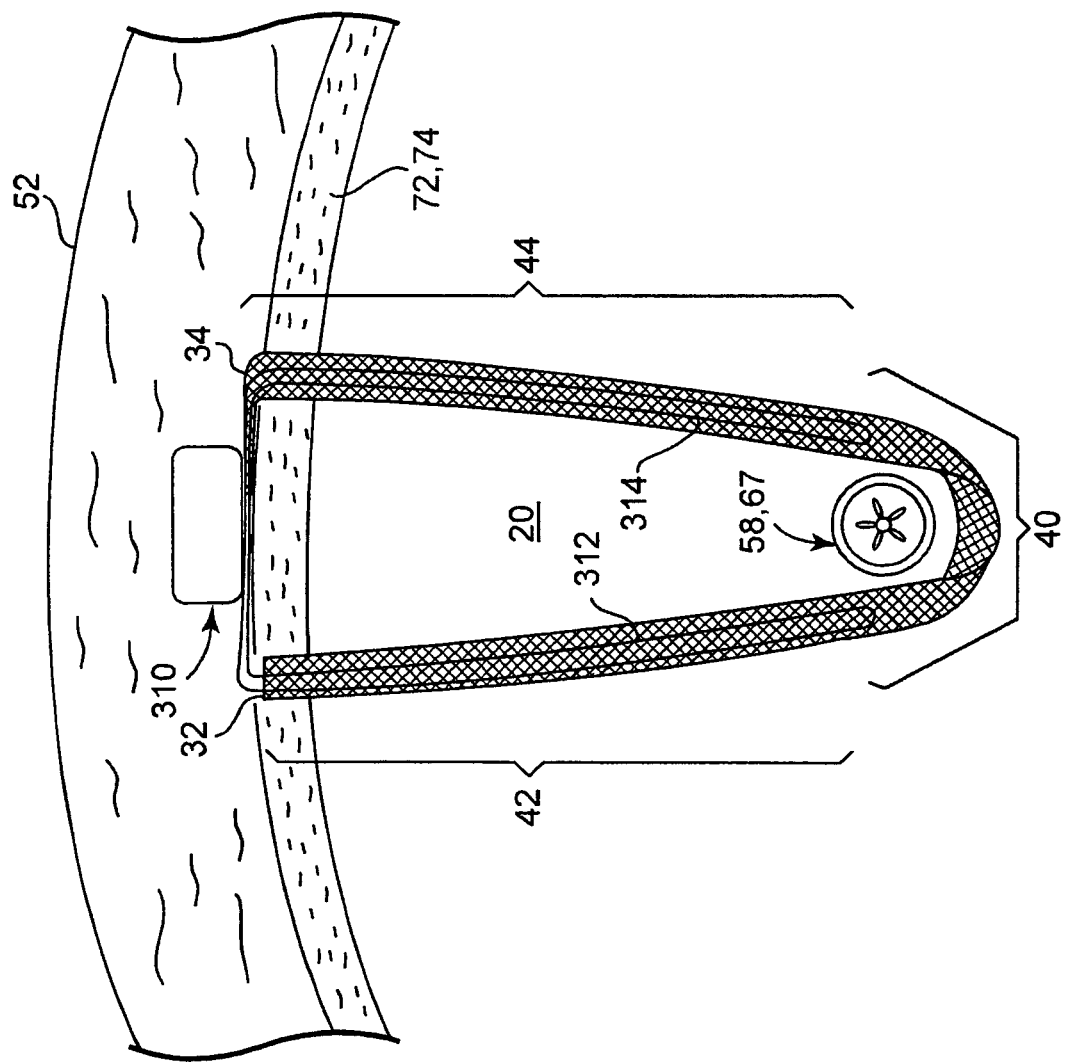

ADJUSTABLE TENSION INCONTINENCE SLING ASSEMBLIES

RELATED APPLICATIONS

This application claims benefit from International Application No. PCT/US2007/014780, having PCT Publication No. WO 2007/149593 A2, which was filed on 22 Jun. 2007, which in turn claims priority to U.S. Provisional Application Ser. No. 60/805,544 filed Jun. 22, 2006, and U.S. Provisional Application Ser. No. 60/806,664 filed Jul. 6, 2006, the entire contents of which are incorporated herein by reference.

TECHNICAL FIELD

The present invention pertains to improved methods and apparatus providing support to a portion of the urethra or rectum or anus to alleviate urinary or fecal incontinence and particularly to elongated slings having mechanisms for selectively adjusting the tension applied through the sling to body tissue.

BACKGROUND

Urinary incontinence is a condition characterized by involuntary loss of urine, beyond the individual's control, that results in the loss or diminution of the ability to maintain the urethral sphincter closed as the bladder fills with urine. Male or female stress urinary incontinence (SUI) occurs when the patient is physically or emotionally stressed. Such patients may also experience urge incontinence.

Fecal incontinence is a condition characterized by involuntary defecation or passage of feces through the anal canal due to injury to or weakness of one or more of the internal anal sphincter, the external anal sphincter, and the levator ani.

Implantable urethral and anal prosthetic sphincter systems have been disclosed in the prior art to treat incontinence that comprise an inflatable balloon that is either pillow or cuff shaped, a balloon reservoir/pressure, source filled with a fluid, a pump, and interconnecting tubing. The balloon is implantable beneath or surrounding the urethral tract (at or near the bladder neck in female patients) or the external anal sphincter and is coupled through tubing to the balloon reservoir/pressure source and pump that are implanted subcutaneously. The pump may be manually actuated to inflate the balloon compress the urethral tract to prevent incontinence and to deflate the balloon to allow voiding. Examples of such prosthetic sphincter systems are disclosed in U.S. Pat. Nos. 4,222,377, 4,571,749, and 5,562,598, and one such system comprises the AMS-800 Urinary Control System available from American Medical Systems, Inc.

Urethral tapes or slings have been developed that are implanted in a urethral sling procedure in which the urethral sling is inserted beneath the urethra and advanced in the retro pubic space, perforating the abdominal fascia. In one procedure, peripheral or end portions of the elongated urethral sling are affixed to bone or body tissue, and a central support portion of the elongated urethral sling extends under the urethral or bladder neck to provide a platform that compresses the urethral sphincter, limits urethral distension, and pelvic drop, and thereby improves coaptation. Elongated "self-fixating" slings have also been clinically introduced for implantation in the body that do not require that the end portions be physically attached to tissue or bone and that rely upon tissue ingrowth into sling pores to stabilize the sling as disclosed, for example, in commonly assigned U.S. Pat. Nos. 6,382,214, 6,612,977, 6,641,524, 6,648,921, 6,652,450, 6,702,827, 6,802,807, and 6,911,003 and publications and patents cited therein.

The above-described slings comprise a central portion that is adapted to support the urethra, two end portions bracketing the support portion, a protective sheath or sheaths encasing at least the end portions, and connectors at the ends of the sling. Various ways of attaching a sleeve end and sling mesh end to a connector are detailed in the above-referenced '450 patent, for example. Further ways of attaching sling ends to sling implantation tools are disclosed in U.S. Patent Application Publication Nos. 2004/0087970, 2005/0245787, and 2005/0250977. The sling implantation tools are employed to form tissue pathways extending from a vaginal incision to two abdominal skin incisions and to draw the sling end portions through the pathways to dispose the sling free ends out of the skin incisions and the central portion around the urethra. The connectors are detached from the sling ends, and the sheaths are drawn out of the skin incisions, allowing the incisions to be closed.

Sling tension is typically adjusted at implantation sufficiently to take up any slack in the sling and impart at least a degree of increased tension to the urethra with the bladder empty. A surgical instrument may be placed between the sling central portion and the urethra, the sling ends drawn to tension and fully close the urethral tract, and the instrument withdrawn so that the uethra is relaxed sufficiently to function. Alternative tension adjustment techniques that may be employed during implantation are disclosed in the above-referenced commonly assigned '827 and '921 patents:

Typically, such urethral tapes or slings are fabricated of a loose weave sling fabric or mesh that acutely engages tissue and encourages tissue ingrowth along the pathway through mesh pores to achieve chronic stabilization or "self-fixation. Tissue ingrowth takes about 2-3 weeks in the typical patient in the absence of any significant intentional or unintentional movement of the mesh. During this post-operative time, the patient monitors the degree of success achieved in ameliorating leakage and any discomfort that might occur if the applied tension is so high as to unduly slow voluntary urination.

If any such problems occur, it may be necessary to reopen the incisions to access and pull on the sling ends to tighten the sling central portion around the urethra or to reopen the vaginal incision to pull on the sling central portion to loosen the sling central portion around the urethra. Several approaches have been taken to simplify or reduce the need for such post-operative adjustments.

One tension adjustment complication arises from the fact that the loose weave sling mesh inherently stretches and elongates when tension is applied at the ends or central support portion to overcome resistance of the tissue bearing against the sling mesh along the tissue pathway. It is difficult to judge just how much tension to apply to achieve adequate tightening or loosening in the central support portion. In one approach to overcoming this complication disclosed, for example, in the above-referenced '450 patent, an elongated repositioning means, e.g., an elongated inextensible tensioning member, is incorporated extending in or along the sling mesh from near the sling ends to or through the sling central portion. Tension applied to the repositioning means is transmitted along the length of the sling so the sling mesh does not substantially stretch during initial positioning and any repositioning during the acute healing phase.

In another approach disclosed, for example, in U.S. Patent Application Publication 2006/0058574 (FIGS. 4a-4f), an expandable member or container is incorporated on or in the sling central support portion that can be inflated or deflated with bulking agent to apply more or less tension to the urethra. As stated therein, optionally, the container has a touchable internal valve element to permit the surgeon to palpate the area prior to injecting or removing the bulking agent. Alternatively, the bulking agent may be injected and removed via a two-way external port. When a bulking agent is injected into the container, the tissue between the mesh and urethra will expand. This results in two effects; a simple vertical lifting due to expansion and a vertical lifting due to stretching the outside of the mesh. A suitable bulking agent may be water or saline. A similar approach is disclosed in U.S. Pat. Nos. 4,019,499 and 6,786,861.

Other approaches that enable increasing tension of the sling central portion against the urethra involve shortening the lengths of the sling end portions as described, for example in the above-referenced, commonly assigned '921 patent. Mesh folds are formed in the sling end portions using filaments that extend through vaginal incisions externally of the body. Depending on the embodiment, the mesh folds can be released to decrease sling tension or be tightened to increase sling tension by pulling on the filament ends following the initial implantation procedure. In other embodiments, filaments are extended substantially through the lengths of the sling end portions and extend from the vaginal incisions. The filaments may be gripped and pulled to tighten the mesh in the sling end portions to increase overall sling tension.

In still another approach disclosed, for example, in U.S. Patent Application Publication 2006/0058574 (FIGS. 5a-5c), the mesh sling or tape is further modified to include a mechanical adjustment means to adjust the length of the tape in the end portions on either side of the central portion after the tape has been implanted in the tissue pathways. The mechanical adjustment means incorporate a tie-wrap mechanism or sutures and one-way suture retaining devices of the type disclosed in U.S. Pat. No. 5,669,935 located along the tape on either side of the central portion. In each case, one suture end is affixed to the tape and extends along it and through a suture retaining device affixed to the tape closer to the central portion. The sutures or tie-wrap are not tensioned at implantation, and the tie-wrap or suture free ends extend through the vaginal incision. If the tension on the urethra is too light as determined during the acute healing phase, the surgeon may grasp and pull on the tie-wrap or suture free ends to shorten the lengths of the tape end portions and thereby increase sling tension. The exposed suture or tie-wrap ends may be severed during chronic implantation.

In yet another approach, tape or sling ends or the end of a tensioning cable coupled to a urethral support mechanism are coupled to a tensioning device that is chronically implanted subcutaneously and can be accessed to adjust sling tension. See, for example, commonly assigned U.S. Pat. No. 4,969,892 and further U.S. Pat. Nos. 5,474,518 and 6,117,067 and the REMEEX® readjustable sling by Neomedic, Intl. (www.remeex.com). Ratchet or gear mechanisms that are accessed using a driver inserted through the skin and thereby rotated to increase or decrease sling tension are disclosed in the '892 and '518 patents. An inflatable/deflatable, elastic chamber, mechanism that incorporates a fill port that is penetrable by a syringe needle advanced through the skin is disclosed in the '067 patent. The adjustment forces are applied to the sling ends and must be transmitted through the sling to effect any change in tension along the sling central portion adjacent the urethra.

Further sling tension adjustment and maintenance techniques involve adding tensioning filaments to the sling free ends and extending the elements through the skin incisions and into engagement with buttons or pads implanted subcutaneously engaging a muscle or rectus fascia layer and/or having tissue engaging elements or anchors along the filament that engage subcutaneous tissues as disclosed, for example, in U.S. Pat. No. 6,911,002 and in U.S. Patent Application Publication Nos. 2005/0004576 and 2006/0089525.

Although effective in alleviating SUI, further improvements in urethral and fecal slings to post-operatively adjust tension applied to the urethra or anus are desirable.

SUMMARY

The preferred embodiments of the present invention incorporate a number of inventive features that address problems in the prior art that may be combined as illustrated by the preferred embodiments or advantageously separately employed.

The present invention involves improvements in an elongated incontinence sling, or simply sling, comprising a central support portion and end portions extending from the central portion to sling ends. Herein, use of the term sling or the expression "incontinence sling" without further qualification shall embrace urethral slings adapted to be placed through a tissue pathway disposing the central support portion between the urethra or bladder neck (hereafter collectively referred to as the urethra for convenience) and the vaginal wall to alleviate urethral incontinence and fecal slings adapted to be placed through a tissue pathway disposing the central support portion inferior to the anus, the anal sphincter or the lower rectum (hereafter collectively referred to as the anus for convenience) to alleviate fecal incontinence. Certain embodiments employ tensioning filaments or lines or cables or sutures that are referred to as "sutures" for convenience.

In accordance with the present invention, such slings are improved to enhance post-operative sling adjustment of the tension applied to the urethra or anus to enhance efficacy and patient comfort. The various embodiments disclosed herein are applicable to both males and females, to address issues of incontinence in both, to address issues of prolapse repair in female and perineal floor descent, as well as fecal incontinence in both. Also surgical techniques such as forming suprapubic, retropubic, transobturator, inside out, outside in tissue pathways between two skin incisions, or a tissue pathway formed from a single incision through the vagina or perineal floor (in male or female patients) are also contemplated for passage of a sling therethrough.

In one preferred embodiment of a sling of the present invention, a sling adjustment mechanism is incorporated into or on a section of one or preferably both of the sling end portions proximal to but spaced from the central support portion that can be adjusted at least in the acute post-operative healing phase to directly adjust tension of the end portions and indirectly adjust tension of the central support portion. The spacing of the sling adjustment mechanism from the central support portion is selected in relation to the patient's anatomy to facilitate access or engagement with an externally applied adjustment actuator or an actuator element extending percutaneously from a skin incision and to effectively transmit tension along the sling to the central support portion. The adjustment mechanisms are generally adjusted to adjust the length and/or tension of the end portions to thereby tension the center support portion and draw it closer to the urethra or anus or to relax tension of the center support portion to release pressure on the urethra or anus.

In certain embodiments, the sling adjustment mechanism comprises one or more suture extending from a point of attachment with one or more of the sling end portions to a suture free end and a sling tensioning device coupled to the suture free end that can be manipulated to increase or decrease sling tension.

In certain embodiments, the sling adjustment mechanism alternatively or further comprises mesh folds formed of sections of the sling mesh In the sling end portions that define adjustment spacings, and tensioning sutures that are stitched through mesh pores of the mesh folds to maintain the mesh fold during implantation and to function as draw strings for later adjustment during the acute healing phase. In certain embodiments, the suture free ends are adapted to be extended through skin incisions during implantation thereby enabling manual tension adjustment during the acute healing phase. The suture free ends may be grasped and pulled to pull the sling folds tighter together to decrease the adjustment spacing and thereby decrease the sling length and increase tension applied by the center support portion to the urethra.

In one variation, the sling tensioning devices incorporated into the sling end portions or sling free ends that extend percutaneously through the skin incisions made to install the sling to enable application of tension to or to release tension during at least in the acute post-operative healing phase to directly adjust tension of the end portions and indirectly adjust tension of the central support portion. For example, sutures extending from the subcutaneously implanted sling free ends are extended through the skin incisions made in the implantation of the sling to be manipulated by pulling or twisting during the acute post-operative healing phase to directly adjust tension of the end portions and indirectly adjust tension of the central support portion.

In other preferred embodiments, a tensioning band extends along at least a section of the sling end portions to apply sling tension along the section by or twisting the band. The free end of the band may be coupled to tensioning devices outside the patient's body.

The suture or band free ends and any tensioning devices coupled thereto may be severed at the skin incisions following adjustment.

In certain preferred embodiments, the sling end portions may be implanted within biodegradable sheaths that make it possible to more easily pull upon or twist the sling end portions until the sheaths dissolve in the body. In other embodiments, the tensioning suture(s) are extended through the lumens of tubes that make it possible to more easily pull upon or twist the sling end portions. The tubes may be biodegradable in the body.

In a further aspect of the invention, the sutures extending from the sling free ends of each of the embodiments disclosed herein are coupled to one or more sling tensioning devices that are subcutaneously implanted in abutting relation to a supporting tissue such as the rectus fascia or the transobturator membrane that the tissue pathway is formed through. Post-operative adjustment of sling tension is contemplated by operating the tensioning device(s) through use of an external adjustment actuator. For convenience, such subcutaneous muscle layers, the rectus fascia or the transobturator membranes or other membranes and fascia are simply referred to as "tissue layers" herein.

In a preferred embodiment of this aspect of the invention, the tensioning device(s) comprises a rotatable bobbin that the suture(s) extends around and that can be rotated to release or draw in a length of suture(s) thereby decreasing or increasing sling tension. In one embodiment, the external adjustment actuator is a tool that is inserted percutaneously (penetrating the skin) to engage and operate the sling adjustment mechanism to increase or decrease the adjustment spacing. Alternatively, it is possible to dissect down to adjustment mechanism.

Various sling tensioning devices are provided that can be rotated by the tool in one direction to draw the sling intermediate ends together to increase sling tension and that can be rotated in the other direction to allow the sling intermediate ends to separate apart to decrease sling tension.

In certain embodiments, a tissue anchor is coupled to at least one sling end adapted to be passed through body tissue to anchor the sling end against a tissue layer to stabilize the sling end and facilitate adjustment of sling tension.

Thus, the sling tension adjustment mechanism comprises one or more of a sling tensioning suture or band, a tensioning device coupled to a suture or band free end, a tissue anchor coupled to one or more of a suture free end and a sling end, a mesh fold, a suture tube, and a sling sheath in various combinations.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 25 is a schematic illustration of a further variation of the adjustable tension sling of the present invention, wherein sutures extend through the sling end portions to be extended though a tissue layer to a sling tensioning device for subcutaneous implantation abutting the tissue layer using an external adjustment actuator adapted to penetrate the skin to engage and operate the sling tensioning device.

Figure 1:
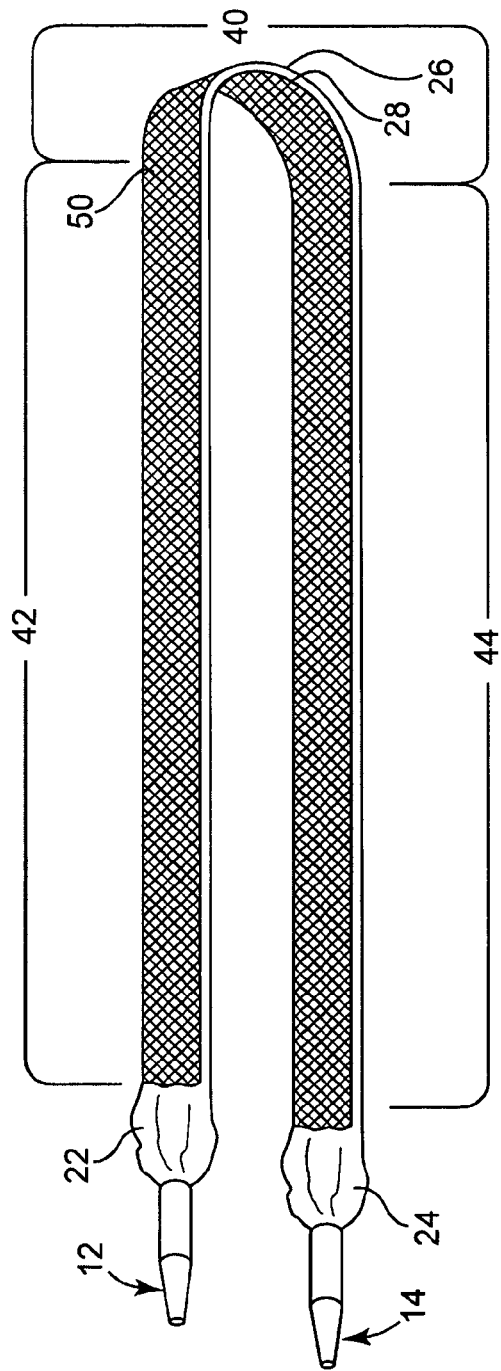
FIG. 1 is a schematic view of an exemplary sling assembly enclosing a sling adapted to be modified in accordance with the invention to function as an adjustable tension urethral or fecal sling.

The drawing figures are not necessarily to scale.

DETAILED DESCRIPTION OF PREFERRED EMBODIMENTS

The various embodiments of the present invention are implemented in slings suitable for and methods of implanting such slings in the treatment of male and female urinary and fecal incontinence and to effect pelvic floor, perineal floor, and pelvic proplapse repairs employing a variety of surgical approaches. For example, female pelvic floor repair slings may be implanted by techniques that involve transvaginal, transobturator, suprapubic, pre-pubic, or transperineal exposures or pathways, and male urinary incontinence slings may be implanted by techniques that involve transobturator, suprapubic, or transperineal pathways. Any of the disclosed embodiments can be used as fecal incontinence slings which may be implanted by techniques that involve transvaginal, transobturator, suprapubic or via perineal floor pathways. In fecal incontinence applications, the disclosed embodiments can be used to correct the anorectal angle in the rectum to re-establish continence in patients. The above methods can, but are not necessarily limited to, utilize helical needles of the type described in U.S. Pat. No. 6,911,003 or C-shaped needles or elongate needles of the type used to perform suprapubic procedures.

Referring to FIG. 1, an exemplary embodiment of an elongated sling assembly 10 is depicted in which the embodiments of the present invention may be advantageously implemented. The elongated sling assembly 10 contains a sling 20 that may be implanted in any of the above-described manners and pathways through which at least end portions of the elongated sling assembly 10 is drawn to dispose a central support portion 40 of sling 20 in operative relation to the urethral or bladder neck or around the anal sphincter or elsewhere in the pelvic region. The sling assembly 10 comprises the sling 20 coupled to sling end connectors 12 and 14 and encased in protective sheaths 22 and 24.

The depicted exemplary sling assembly 10 thus extends between sling end connectors 12 and 14 that engage with the free ends of right hand and left hand sling implantation tools (non-suprapubic) of the types described above, for example. The sling end connectors 12 and 14 are shaped to dilate the right and left passages or pathways through body tissue formed by the curved needles of the right and left hand implantation tools in the above-described trans-vaginal or transobturator procedures, for example.

In this example, the sling 20 is enclosed within protective sheaths 22 and 24 extending from the sling end connectors, 12 and 14, respectively, to respective free and open sheath ends 26 and 28. Preferably, the protective sheaths 22 and 24 are constructed of a flexible thin transparent plastic film that enables visual examination of the sling 20 and is sufficiently lubricious that it passes easily through the tissue pathways of the patient formed using the right hand and left hand sling implantation tools (non-suprapubic) of the types described above or otherwise created. The sheaths 22 and 24 can include sheath indicia or tear scores, perforations or holes for assisting the surgeon in properly orienting sling 20 relative to the urethra. Certain embodiments of the present invention involve modifications of the sheaths 22 and 24.

Figure 2:
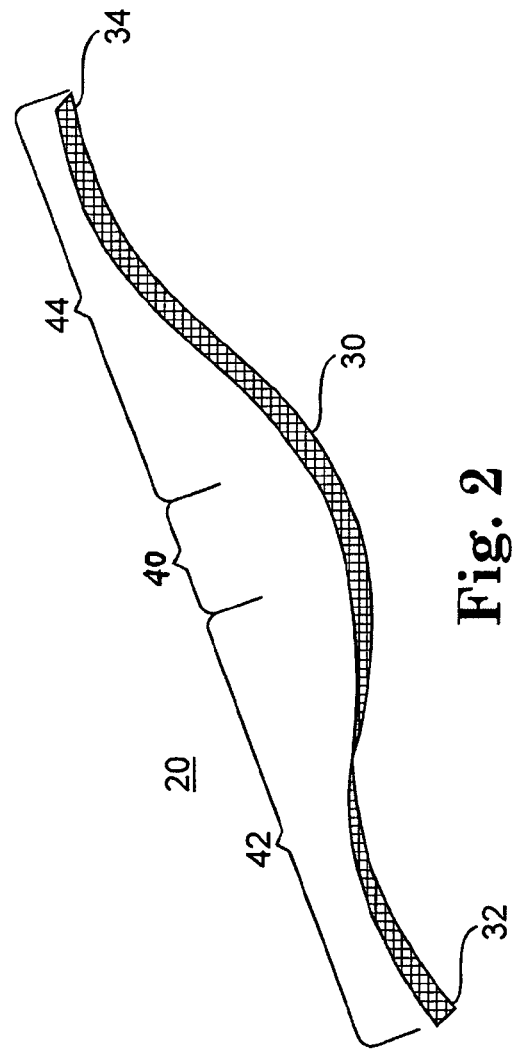
FIG. 2 is a schematic illustration of the sling of FIG. 1 adapted to be modified in accordance with the invention to provide an adjustable tension function.
Figure 3:
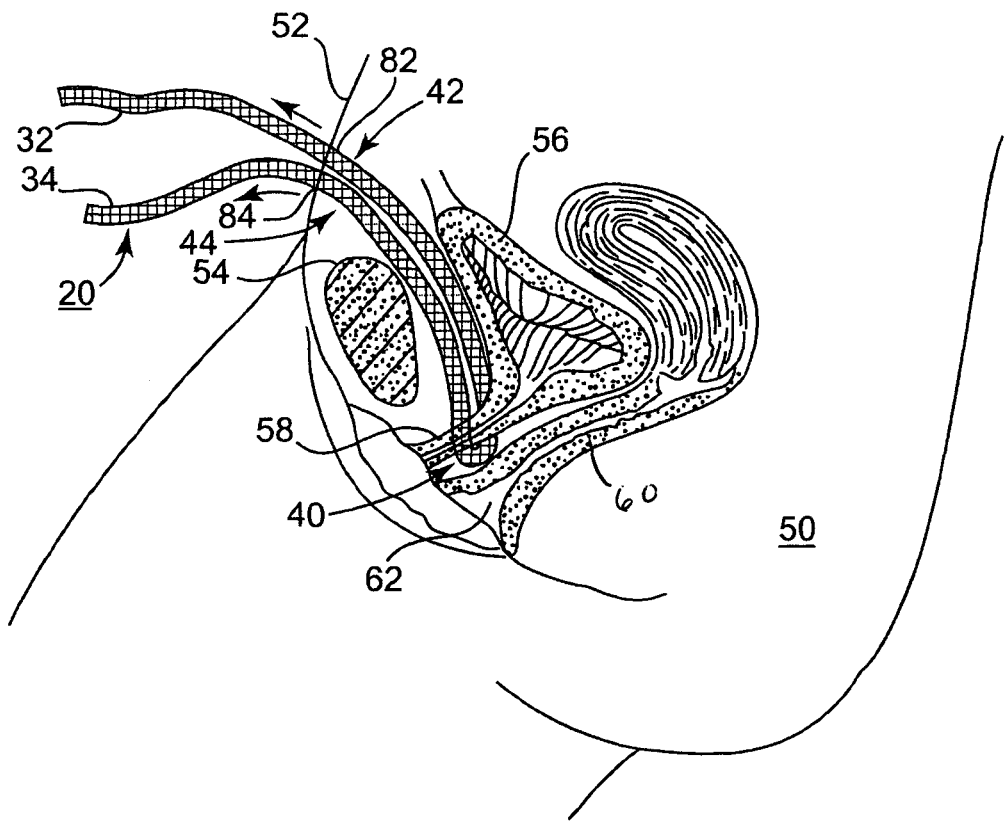
FIG. 3 is a schematic illustration of the sling of FIG. 2 implanted in a female patient's body in relation to the urethra or bladder neck to function as a urethral sling.

The sling 20 that is left in place chronically (following implantation and removal of sheaths 22 and 24 and end connectors 12 and 14) comprises an elongated, rectangular (in this depicted embodiment) braided or preferably knitted, mesh strip or simply mesh 30 as shown in FIG. 2. The sling 20 and mesh 30 are subdivided into a central support portion 40 that is adapted to be placed through a pathway extending between the urethra or bladder neck and the vaginal wall. Proximal end portions 42 and 44 of sling 20 extend from the central support portion 40 to the mesh ends 32 and 34. In FIGS. 1-3, the mesh 30 extends between mesh ends 32 and 34 and may be continuous throughout the length of the sling 20 between mesh ends 32 and 34. The attachment may be a direct attachment as depicted or, alternatively, an indirect attachment, e.g., by sutures extending between ends of sections of the mesh 30 or other materials forming the sling central support portion 40 and the sling end portions 42 and 44. In certain embodiments, the central portion 40 may be formed of any tissue-compatible synthetic material or any natural biocompatible material, including, but not limited to, treated autologous, allograft, or xenograft tissues, porcine dermis, a tissue engineered matrix, or a combination thereof.

The sling 20 of sling assembly 10 is therefore similar to those the disclosed in the above-referenced '450 and '003 patents but is modified herein to incorporate one or more of the aspects of the present invention. It will be understood that the mesh 30 may be dimensioned shaped in a variety of ways known in the art for implantation in the treatment of male and female urinary and fecal incontinence and to effect pelvic floor, perineal floor, and pelvic proplapse repairs employing a variety of surgical approaches. For example, the sling 20 may comprise more than two end portions 42 and 44 coupled to connectors and extending at a variety of angles from a particularly shaped center portion 40.

In the implantation procedures described in the above-referenced '214, '450, and '524 patents and U.S. Patent Application Publication Nos. 2005/0043580 and 2005/0065395, the sling connector ends 12 and 14 are fitted to the implantation tools and the proximal end portions 42 and 44 are drawn through the body passageway or pathway. The central support portion 40 is adapted to be drawn against tissue to support the urethra or bladder neck or the anal sphincter or elsewhere in the pelvic region after the proximal end portions 42 and 44 are drawn through body pathways. The sling connector ends 12, and 14 are drawn out of the skin incision and detached from the implantation tool needle ends. The mesh 30 and sheaths 22 and 24 are severed just proximate to the connector ends 12 and 14, respectively. The remaining portions of the protective sheaths 22 and 24 are withdrawn over the mesh 30 and through the skin incisions. The sling 20 then remains in place, and tension adjustments are made to provide sufficient urethral or anal resistance to leakage. The sling can also provide support, in a related embodiment, to the anal sphincter or elsewhere in the pelvic region so as to return the tissue/muscles to its original anatomical position and support it as well. The incisions are closed upon completion of the tests, and tissue ingrowth into the pores of the mesh 30 takes place in a matter of weeks.

Before describing the embodiments of the invention, attention is directed to a step illustrated in FIG. 3 of one such sling implantation procedure that results in the sling 20 extending through a tissue pathway created in a female (for example) patient 50 extending around the urethra 58. In preceding steps, the tissue pathway was formed by passing needles through a vaginal skin incision 62 just adjacent to the vagina 60 through soft tissue between urethra 58 and vagina 60 and along each side of urethra 58 through layers of fat, muscle, and fascia and between pubic bone 54 and bladder 56 to first and second skin incisions through skin 52. Any of the known tissue pathways may be formed in this generally described manner. In a related embodiment, a sling is implanted via a single incision (vaginal incision 62) with the sling being pushed up into the transobturator or retro pubic space. In a related embodiment, the end connectors 12 and 14 of the sling assembly 10 are attached to the same or other needles to draw the sling assembly 10 through the tissue pathway to dispose the end connectors outside the patient's skin 52. As shown in FIG. 3, the connectors 12 and 14 and sheaths 22 and 24 were removed after being drawn out of the skin incisions, leaving the sling 20 in place. In another related embodiment, connectors 12 and 14 are eliminated.

Figure 4:
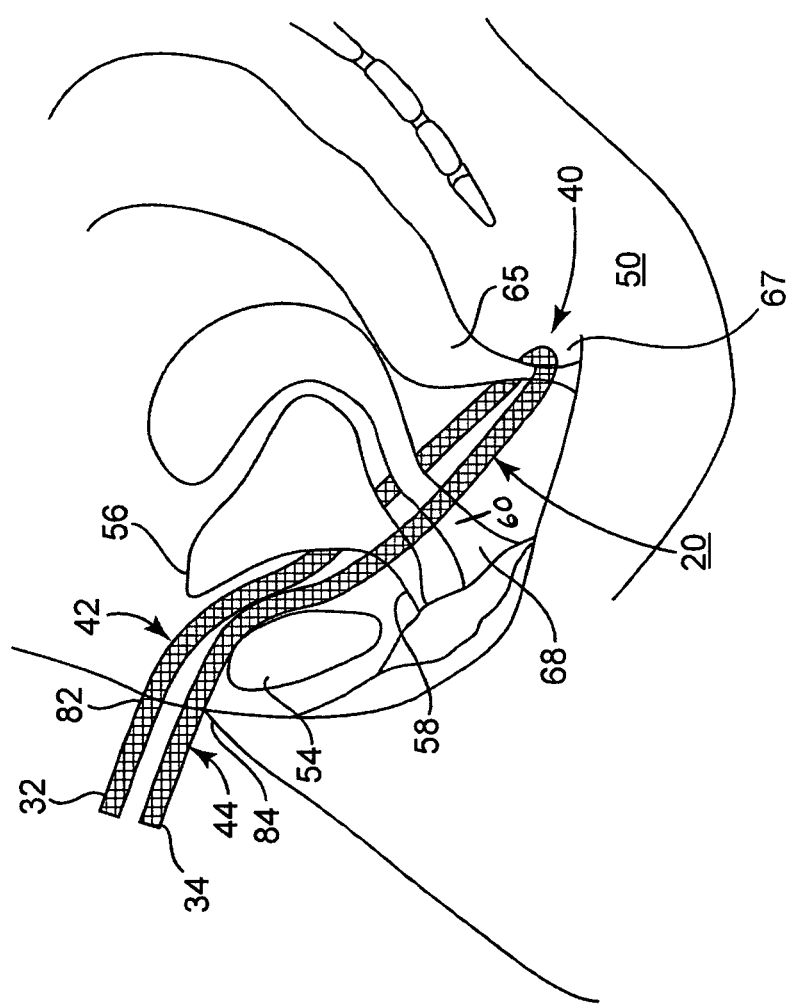
FIG. 4 is a schematic illustration of the sling of FIG. 2 implanted in a female patient's body in relation to the anus and rectum to function as a fecal sling.

Referring to FIG. 4, a schematic illustration of an incontinence sling implanted in a female (for example) patient's body for treating fecal incontinence is depicted. In this illustration, the central support portion 40 extends underneath the anus or anal sphincter 67 or inferior portion of the rectum 65 (hereafter collectively referred to as the anus 67 for convenience) to correct the anorectal angle in the patient. Various surgical approaches can be used to implant sling 20 to correct fecal incontinence including suprapubic, transobturator, retropubic, prepubic, transperineal and transvaginal (including a single incision approach transvaginally or transperineally).

Figure 5:
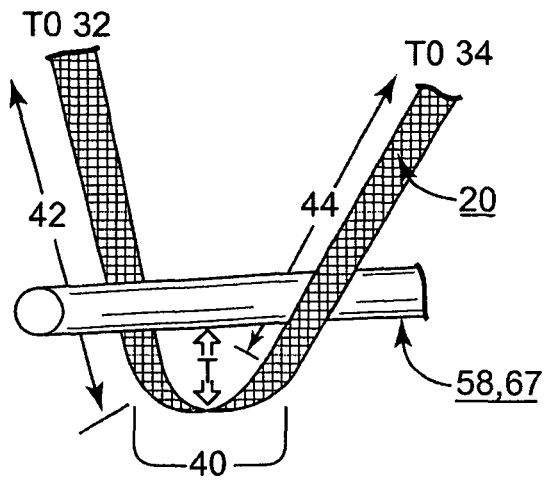
FIG. 5 is a schematic illustration of the relation of the sling central support portion and sling end portions to the urethra or anus.

At this point, the tension T that sling 20 applies against the urethra 58 or anus 67 is adjusted as schematically illustrated in FIG. 5. Since the procedure may be performed using a local anesthesia, the patient 50 is able to provide feedback to the surgeon during adjustment of sling tension. In the procedure illustrated in FIG. 3, typically, the bladder 56 is filled with saline using a catheter, and the patient is requested to cough. The surgeon is able to determine whether leakage occurs and may adjust the tension on the sling 20 by pulling on the exposed sling ends 32 and 34 to increase tension of the center support portion 40 against the urethra 58 or by pulling on center support portion through the vaginal incision to decrease the tension of the center support portion 40 against the urethra 58. The exposed end sections of the end portions 42 and 44 are trimmed away, and the abdominal incisions and the vaginal incision (as well as the labia fold incisions for the transobturator approach) are closed. In the various embodiments of the present invention, such slings as sling 20, are improved to enhance post-operative sling adjustment of the tension T applied to the urethra 58 or the anus 67 to enhance efficacy and patient comfort.

It will be understood that the embodiments of the sling of the invention may be modified by substituting other support materials than open pore mesh 30, particularly in the central support portion 40, e.g., homograft or allograft materials or nonporous synthetic materials. Moreover, other materials and structures may be substituted for the mesh 30 in the sections of constituting one or both of the end portions extending from the intermediate ends 38 and 48 to the ends of the central support portion 40. For example, one or more straight or spiral suture may be substituted for all or part of such sections.

Moreover, the central support portion 40 may take any shape that is found to be most suitable to support the urethral and anal tissues that are to be supported in use of the sling.

While not essential to the practice of the present invention, it may be desirable to provide mechanisms incorporated into or that act on the sling central support portion 40 to facilitate the adjustment of the tension T applied to the urethra 58 or the anus 67. For example, a sling central portion adjustment mechanism may be provided to increase and/or decrease the tension applied locally to the urethra 58 or the anus 67. The sling central portion adjustment mechanism is associated directly or indirectly with the sling central support portion 40 and is distinct from the sling adjustment mechanisms incorporated in the sling end portion or portions. For example, the sling central portion tension adjustment may simply comprise a suture extending around the sling central portion and passing through the skin incision to provide post-operative tension adjustment until the suture is withdrawn through the skin or is absorbed by the body.

Longer-term post-operative adjustment of the sling central portion tension may be accomplished with sling central portion adjustment mechanisms that remain in place. In one approach, the mechanism may be accessed for tension adjustment employing an external adjustment actuator that is percutaneously advanced through the skin 52 to engage the sling central portion adjustment mechanism. For example, one such approach involves injecting or withdrawing fluid from a fluid chamber of a pillow of the sling central portion adjustment mechanism applying pressure to the urethra 58 or the anus 67.

In certain preferred embodiments of the present invention, a sling adjustment mechanism is incorporated into or on a section of one or preferably both of the sling end portions 42 and 44 preferably proximal to but spaced from the central support portion 40 that can be adjusted at least in the acute post-operative healing phase. However, the boundary between the central support portion 40 and the sling end portions 42 and 44 is somewhat arbitrary unless the sling central portion is formed of a different material or has a differing width than the respective material or width of the sling end portions 42 and 44, So it will be understood that the sling intermediate ends described herein as located within the sling end portions or between the sling ends and the sling central portion embraces a location at the junction of the sling end portions 42 and 44 with the central support portion 40. The spacing of each sling adjustment mechanism from the central support portion is selected in relation to the patient's anatomy to facilitate access or engagement with an externally applied adjustment actuator or an actuator element extending percutaneously from a skin incision. The adjustment mechanisms are generally adjusted to adjust the length and/or tension of the end portions 42 and 44 to thereby tension the center support portion 40 and draw it closer to the urethra 58 or anus 67 or to relax tension of the center support portion 40 to release pressure on the urethra 58 or anus 67.

In certain embodiments, the end portion adjustment mechanisms are operated by actuator elements extending percutaneously through skin incisions 82 and 84 in the patient's skin to the sling end portions 42 and 44, respectively. In other preferred embodiments, implantable suture or tissue or sling end anchors or sling tension adjustment mechanisms are coupled to the sling ends to be implanted subcutaneously to maintain sling tension. Certain implantable tension adjustment mechanisms are adapted to be percutaneously accessed with a tension adjustment tool to adjust sling tension during chronic implantation. In certain embodiments, sutures extend from sling adjustment mechanisms incorporated in the sling end portion(s) to such implantable suture or tissue anchors or tension adjustment mechanisms.

Figure 6:
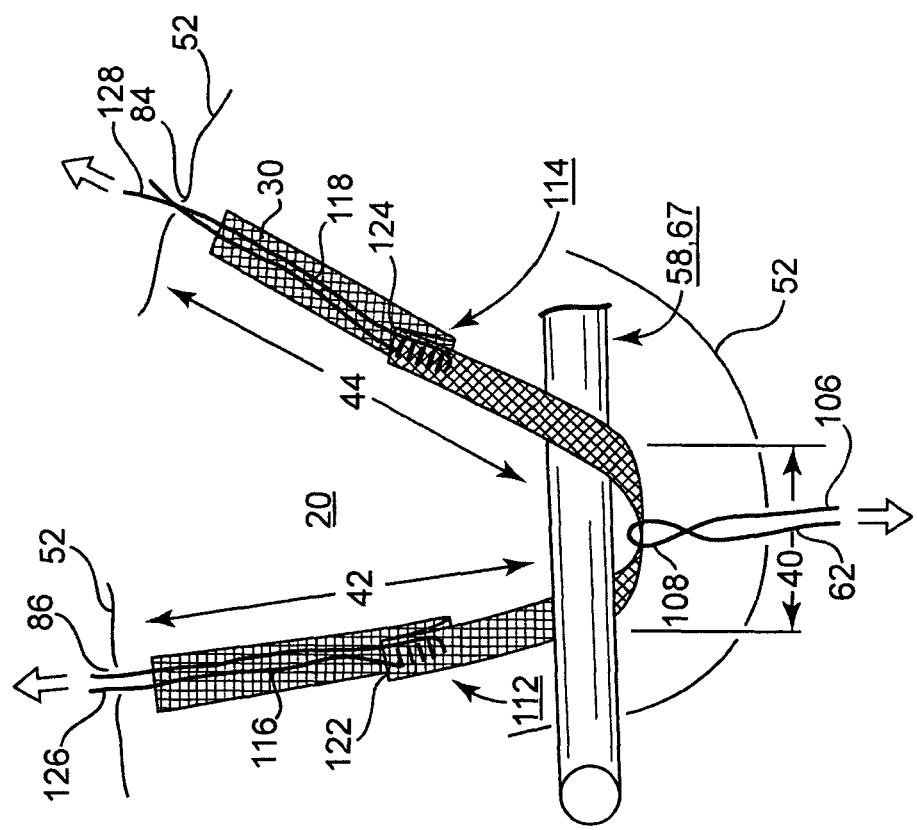
FIG. 6 is a schematic illustration of a first embodiment of an adjustable tension sling of the present invention, wherein mesh fold sling adjustment mechanisms are incorporated into the sling end portions to increase and/or decrease the tension applied locally to the urethra.
Figure 7A:
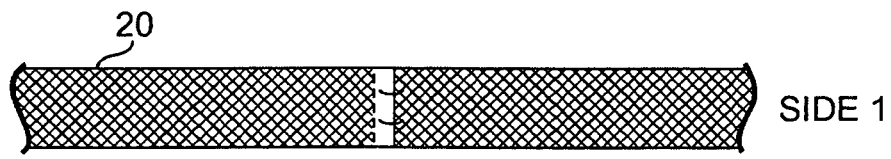
FIGS. 7A-7B, 8A-8B, 9A-9B, and 10A-10B are schematic depictions of mesh folds maintained by sutures passed through the mesh pores in a variety of stitch patterns.
Figure 7B:
Figure 8A:
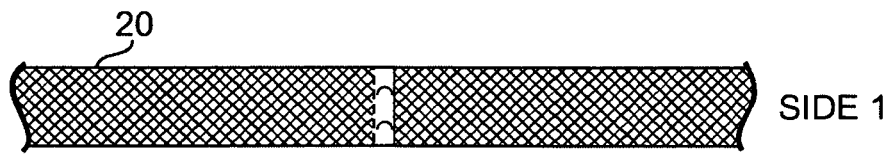
Figure 8B:
Figure 9A:
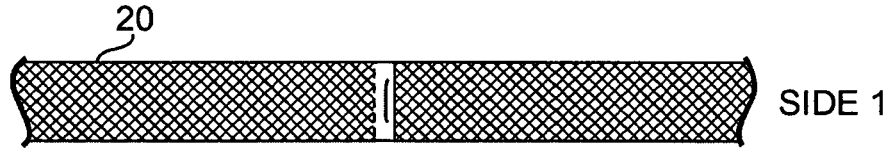
Figure 9B:
Figure 10A:
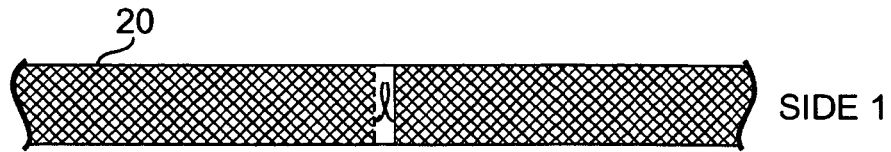
Figure 10B:

A further sling adjustment mechanism can optionally be employed to engage and adjust the tension of the sling 20 at the central support portion 40 in the manner of suture 108 with suture ends 106 extending through vaginal incision 62 operable as described with respect to FIG. 6.

One such embodiment is depicted in FIGS. 6-10, wherein the sling adjustment mechanisms 112 and 114 are disposed along sections of sling end portions 42 and 44. Sections of the sling mesh 30 in the end portions 42 and 44 are folded into folds 122 and 124 to form the respective sling adjustment mechanisms 112 and 114, and adjustment sutures 116 and 118 are stitched through the respective folds 122 and 124 to maintain the fold shape during implantation and to function as draw strings for later adjustment during the acute healing phase. In these embodiments, the suture ends 126 and 128 of respective sutures 116 and 118 extending from the skin incisions 82 and 84 during implantation of the sling 20 function as the adjustment actuators. The suture ends 126 and 128 may be grasped and pulled to shorten the adjustment spacings defined by the lengths of the mesh folds 122 and 124 to thereby shorten the sling end portions 42 and 44 and thereby decrease the sling length and increase tension applied by the center support portion 40 to the urethra 58. In FIGS. 7-10, a variety of stitch patterns for stitching the sutures through the mesh pores to hold them together during implantation. They can be cut or pulled to untie them post-op. In a related embodiment, folds 122 and 124 that may be compressed by tensioning the sutures 116 and 118 are depicted in FIGS. 7A-7B, 8A-8B, 9A-9B, and 10A-10B.

A further adjustment suture 108 (optionally formed of biodegradable material) is optionally placed around the sling mesh 30 and extended through a skin or vaginal incision 62 (for urinary and fecal incontinence) to enable manual tension adjustment. The suture ends 106 may be grasped and pulled to function as an actuator element and pull the sling mesh away from the urethra 58 (or anus 67) to release tension applied by the center support portion 40 to the urethra 58 (or anus 67).

In the absence of adjustment suture 108, the sling central support portion 40 may be accessed by reopening the incision 62 to pull on the sling 20 to draw the sutures 116 and 118 back through the mesh pores, thereby increasing the sling length and decreasing tension applied by the center support portion 40 to the urethra 58 or anus 67.

Optionally, a biodegradable sheath of the type described above may be placed over the folds 122 and 124 to inhibit tissue ingrowth into the mesh pores and ease adjustment of the sling 20 until the sheath is absorbed and tissue ingrowth encapsulates and immobilizes sling mesh 30. Alternatively, in this and other folded mesh embodiments disclosed herein, the mesh 30 in mesh folds 122 and 124 may be coated with a material that inhibits or slows tissue ingrowth, or the sections of the mesh 30 forming mesh folds 122 and 124 may be formed of a material that inhibits or slows tissue ingrowth.

The suture ends 126, 128, and 106 may be severed at the respective incisions 82, 84, and 62 following final adjustment.

Figure 11:
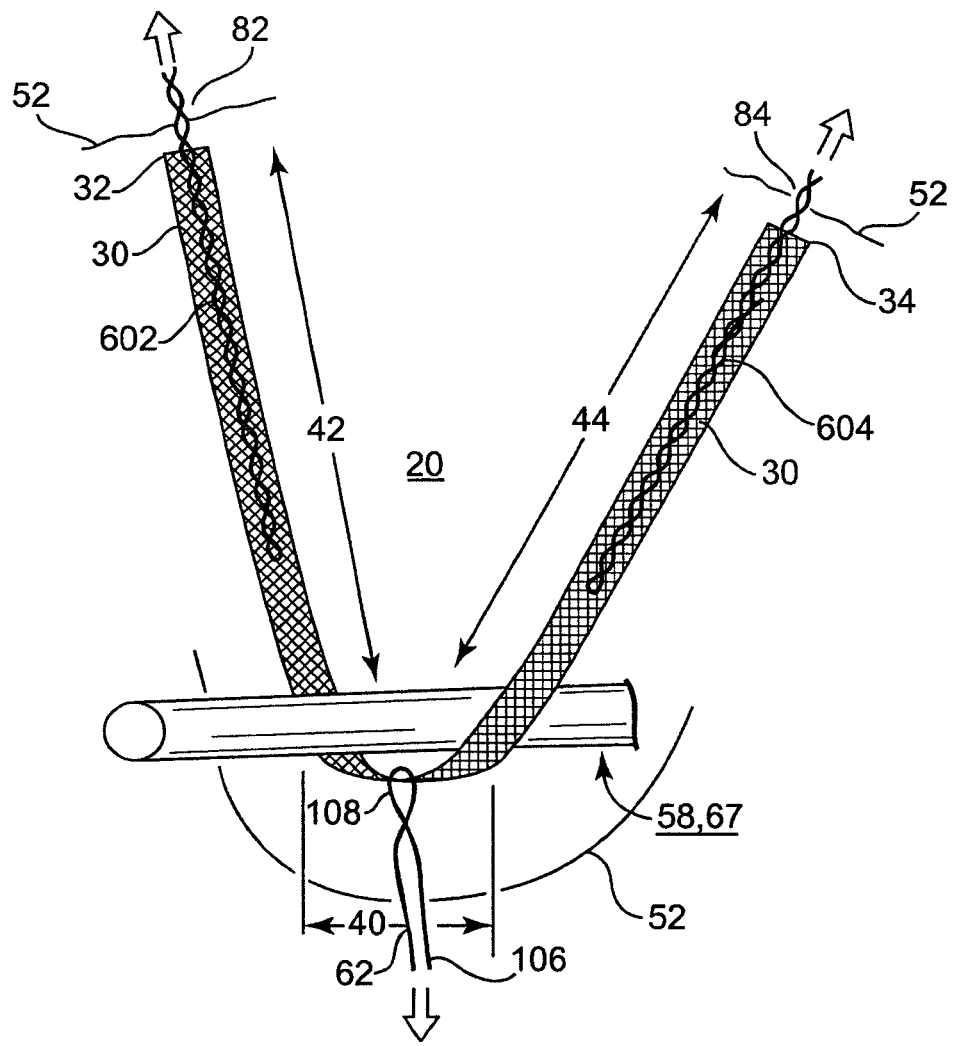
FIG. 11 is a schematic illustration of a further embodiment of an adjustable tension sling of the present invention, wherein mesh adjustment twisted sutures are incorporated into the sling end portions and extend through the skin incisions made to implant the sling providing external suture free ends that can be pulled to increase sling tension.
Figure 12:
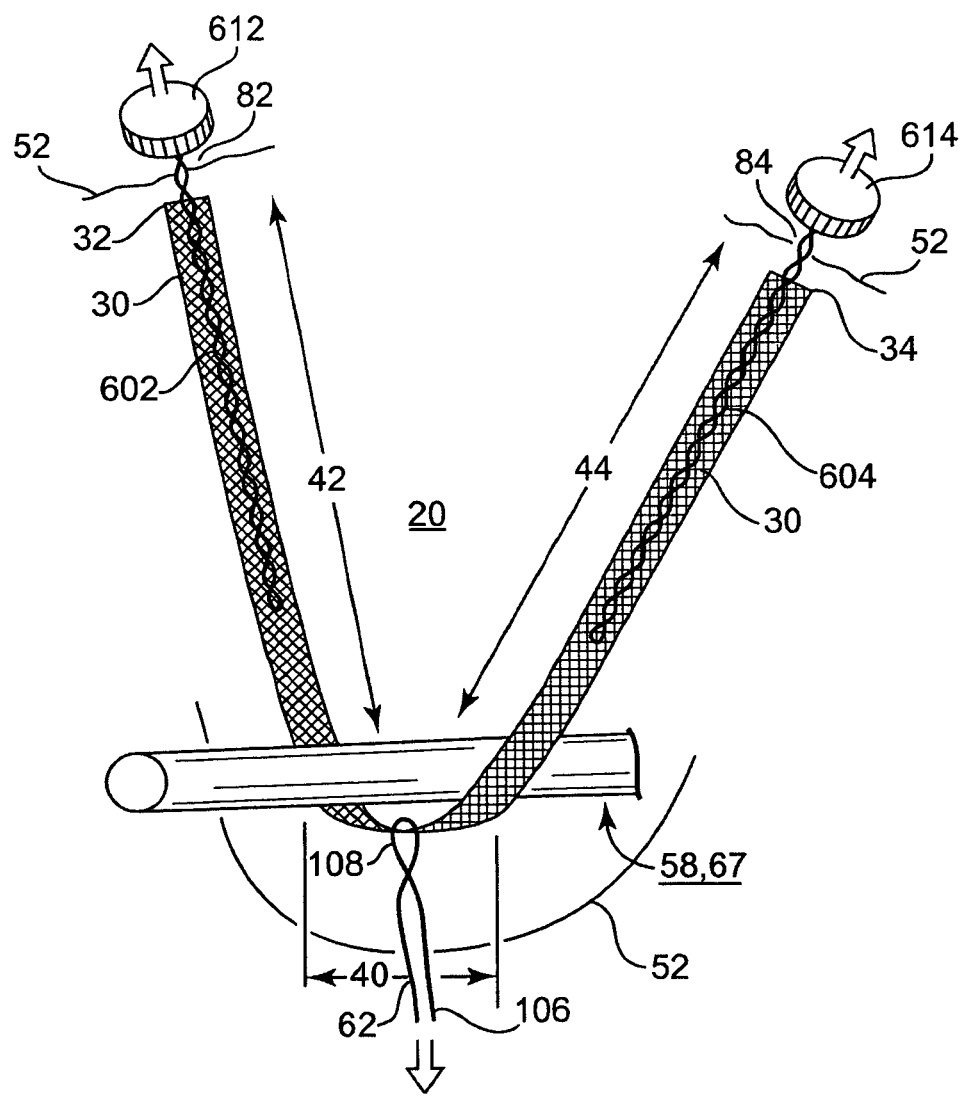
FIG. 12 is a schematic illustration of a modification of the adjustable tension sling of FIG. 11 having buttons coupled to the external suture free ends that can be pulled or released to increase sling tension.
Figure 13:
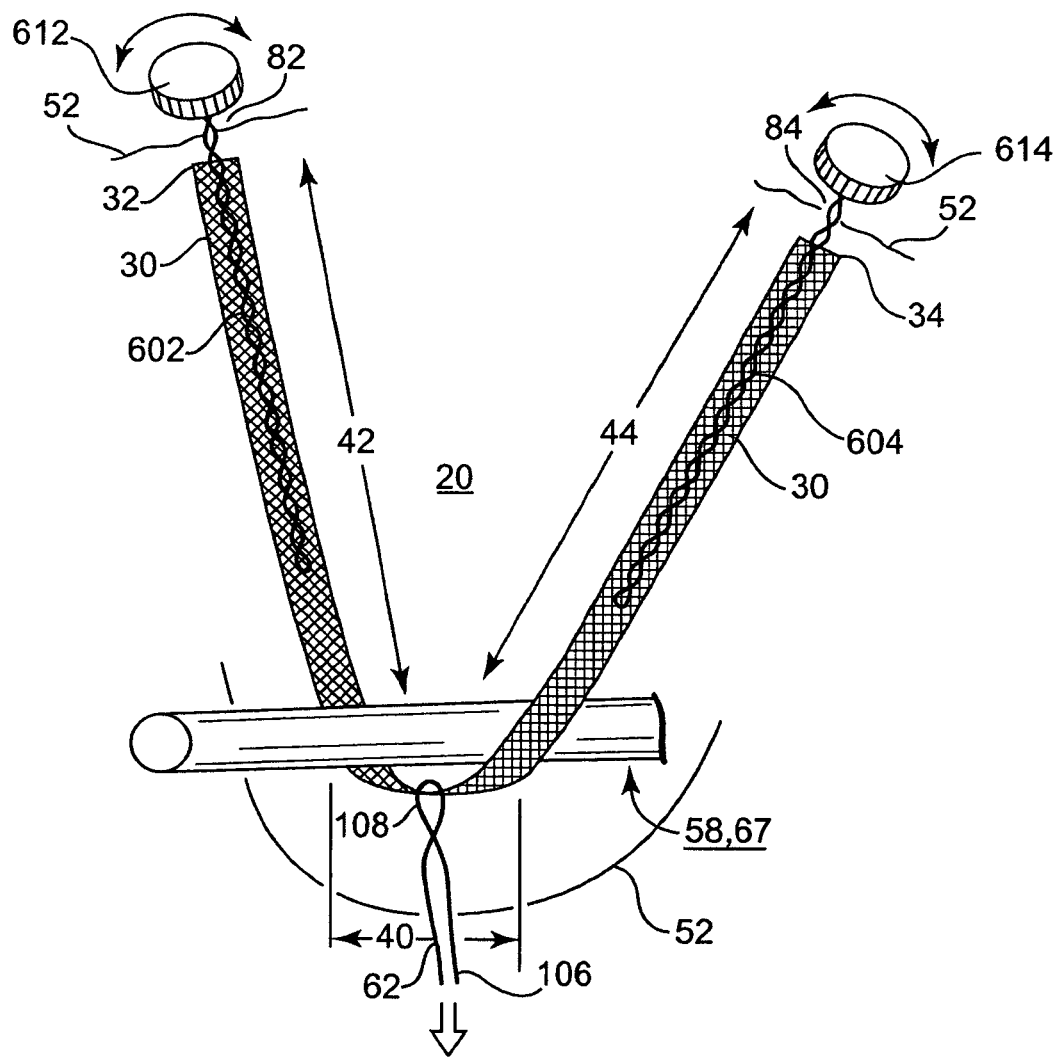
FIG. 13 is a schematic illustration of a modification of the adjustable tension sling of FIG. 12 having buttons coupled to the external suture free ends that can be twisted to increase or decrease sling tension.

Turning to FIGS. 11-13, filaments or sutures 602 and 604 that are preferably biodegradable are looped back and forth through mesh pores and axially along sections of the end portions 42 and 44 and are extended from the subcutaneously implanted sling free ends 32 and 34 to exposed suture free ends. The suture free ends of sutures 602 and 604 may be tied to discs or buttons 612 and 614, respectively. The suture free ends of sutures 602 and 604 or buttons 612 and 614 may be grasped and pulled or rotated during the acute post-operative healing phase to directly increase tension of the end portions 42 and 44 and indirectly adjust tension of the central support portion 40.

Figure 14:
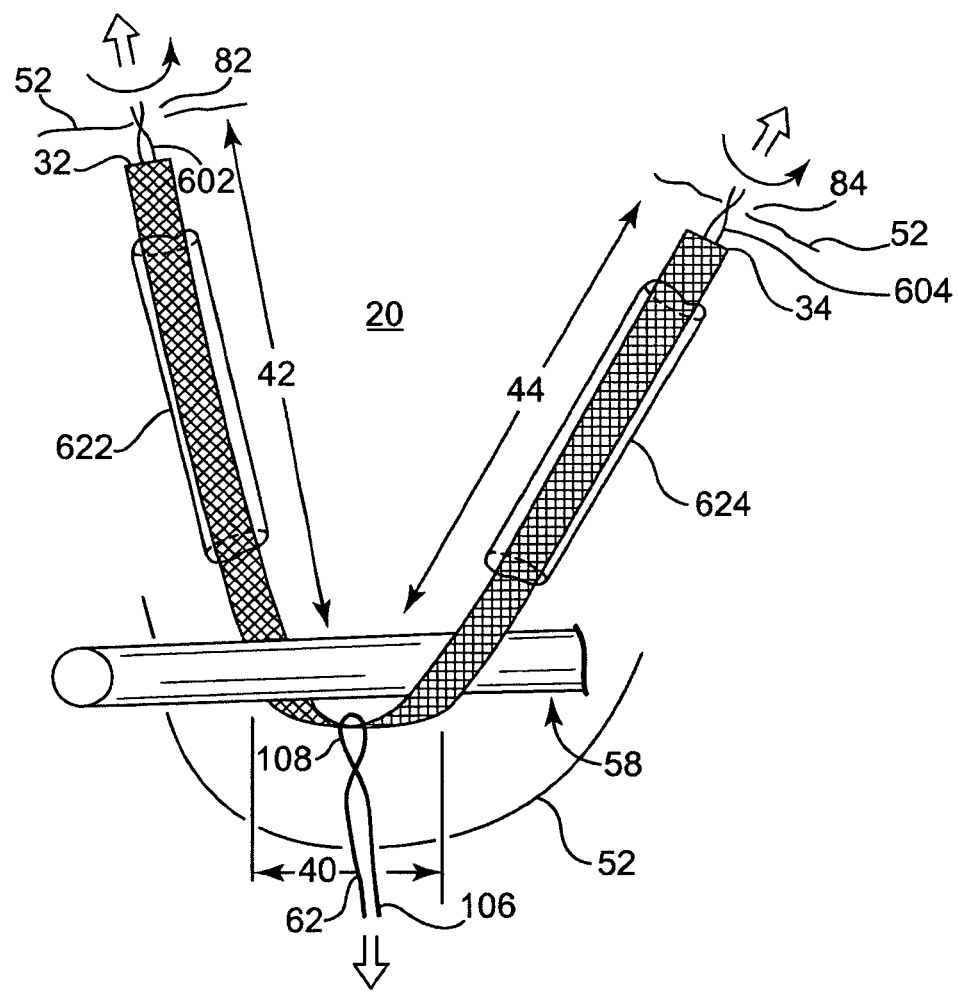
FIG. 14 is a schematic illustration of a modification of the adjustable tension sling of FIGS. 11-13 having sheaths surrounding sections of the sling end portions to inhibit or delay tissue ingrowth to facilitate increasing sling tension by pulling or twisting the external suture free ends.
Figure 15:
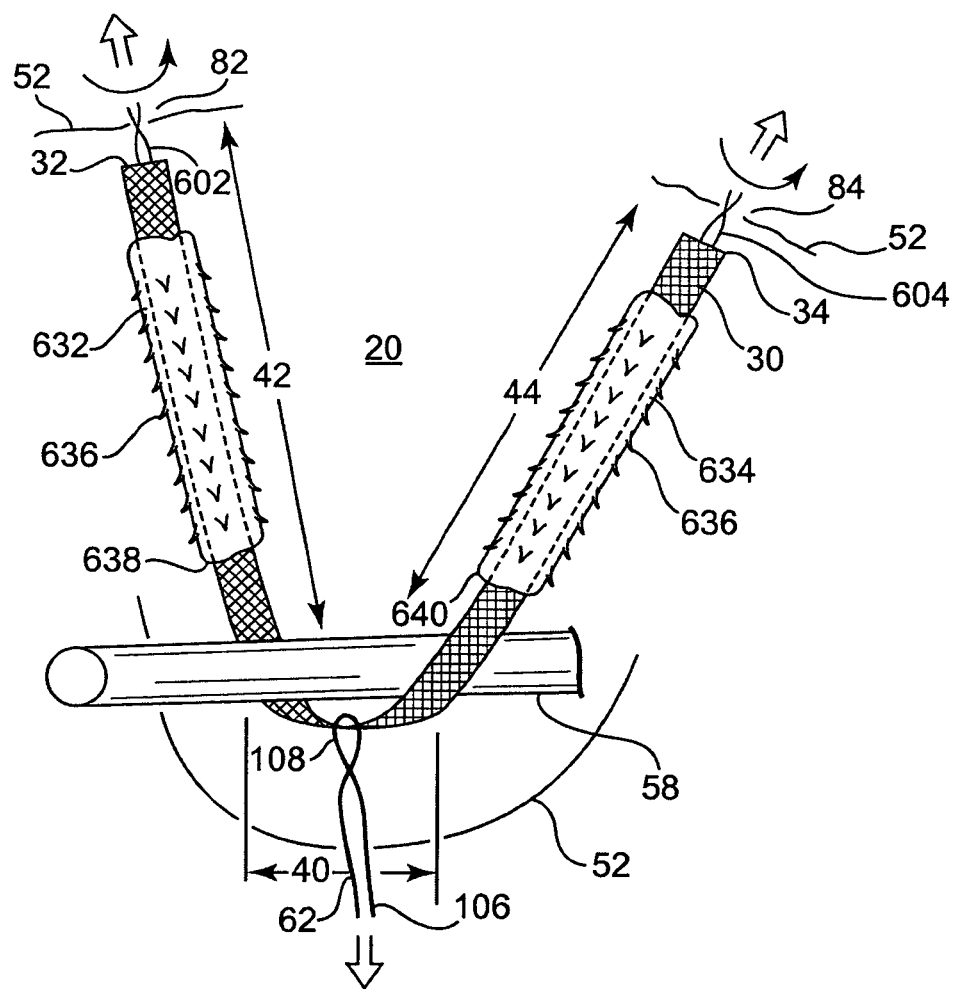
FIG. 15 is a schematic illustration of modifications of the sheaths of FIG. 14 to stabilze the sheaths during the acute post-operative healing phase.

In certain preferred embodiments, the sling end portions may be implanted within biodegradable sheaths that make it possible to more easily pull upon or twist the sling end portions until the sheaths dissolve in the body. Simple open ended, biodegradable sheaths 622 and 624 are disposed around the respective sling 42 and 44 as shown in FIG. 14. More complex, open ended, biodegradable sheaths 632 and 634 are disposed around the respective sling 42 and 44 as shown in FIG. 15. The exterior surfaces of sheaths 632 and 634 are roughened or textured or formed with protrusions 636 that in each case increase frictional engagement with surrounding tissue. The sheaths 622, 624 and 632, 634 block tissue friction from interfering with the application of or attenuating the tension applied to the sling end portions through the pulling or twisting of the sutures 602, 604 as described with respect to FIGS. 11-13. The suture free ends of sutures 602 and 604 may be left exposed or tied to discs or buttons 612 and 614, respectively, of FIGS. 12 and 13.

Preferably, the further adjustment suture 108 placed around the sling mesh 30 and extended through the skin incision 62 is employed to enable manual tension adjustment of the central support portion 40. During such adjustment to release tension applied to urethra 58, the sling mesh 30 may be stretched and pulled from the lumens of the sheaths 622, 624 and 632, 634 toward the urethra 58. The distal end openings 638 and 640 of the respective sheaths 632 and 634 are preferably narrowed to interfere with the sling mesh 30 retracting back into the sheath lumen, thereby helping to maintain the adjustment of the central support portion 40.

Figure 16:
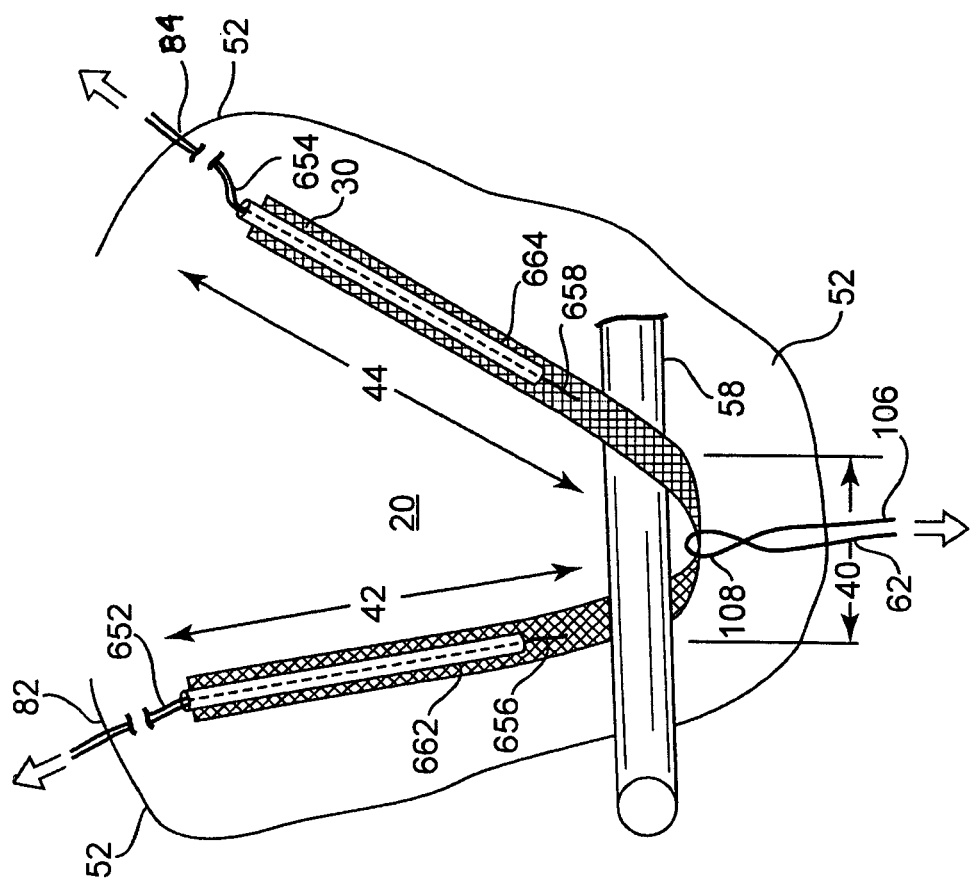
FIG. 16 is a schematic illustration of a further embodiment of an adjustable tension sling of the present invention, wherein tension increasing adjustment sutures are attached to the sling mesh and extended through elongated tube lumens extending alongside sections of the sling end portions and through the skin incisions to external suture free ends that can be pulled to tighten the sling mesh and increase sling tension.

In FIG. 16, filaments or sutures 652 and 654 that are preferably biodegradable are attached at respective fixed ends 656 and 658 to the sling mesh 30 at points along the lengths of the sling end portions 42 and 44 extended through respective tubes 662 and 664 past the sling free ends 32 and 34 and through the skin incisions 82 and 84. The suture free ends of sutures 652 and 654 may be left exposed or tied to discs or buttons 612 and 614, respectively, of FIGS. 12 and 13. The suture free ends of sutures 602 and 604 or buttons 612 and 614 may be grasped and pulled during the acute post-operative healing phase to directly increase tension of the end portions 42 and 44 and indirectly adjust tension of the central support portion 40. The tubes 662, 664 preferably do not buckle during application of pulling force along the sutures 652 and 654 and enable application of the tension to the sling mesh 30 at points closer to the central support portion 40. It will be understood that the suture fixed ends 656 and 658 may be positioned within the central support portion or that the sutures 652 and 654 may comprise a single suture extending along the length of the sling 20 through the tube lumens and across the central support portion. Again, preferably, the further adjustment suture 108 placed around the sling mesh 30 and extended through the vaginal skin incision 62 is employed to enable manual tension adjustment of the central support portion 40.

Figure 17:
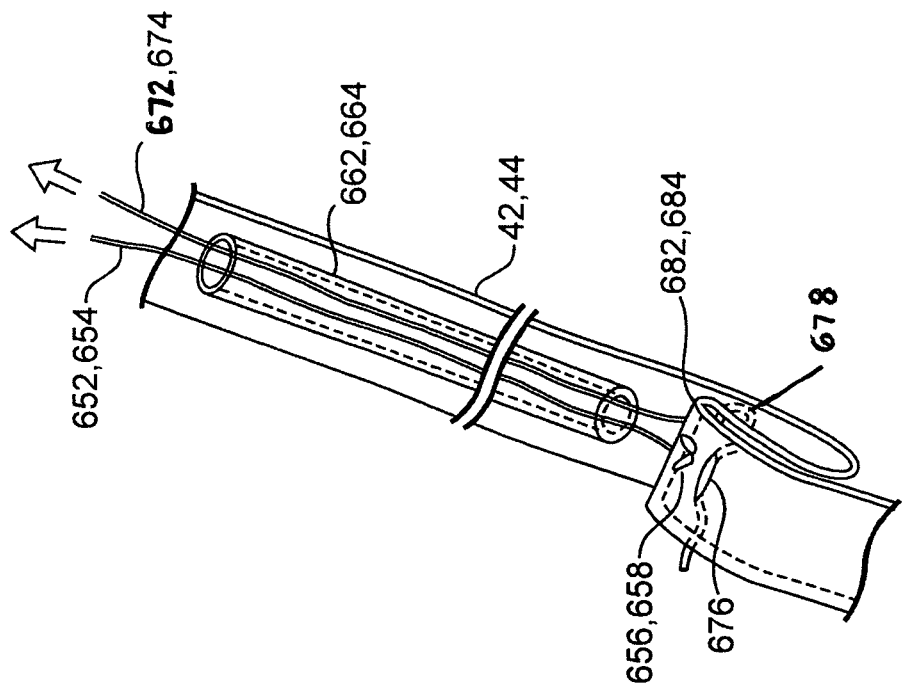
FIG. 17 is a schematic illustration of a modification of the adjustable tension sling of FIG. 16, wherein a mesh fold is formed in the sling mesh and tension reducing adjustment sutures extend through the skin incisions and the tube lumens and are looped through the mesh folds, whereby tension reducing suture free ends may be pulled to release the sling mesh folds and reduce sling tension.

In FIG. 17, the sling 20 of FIG. 16 is modified by inclusion of mesh folds 682 and 684 formed in the mesh 30 of sling end portions 42 and 44 and flexible tubes 662 and 664 extending from the mesh folds 682 and 684 along the respective sling end portions 42 and 44. In addition, a tension increase suture 652 and 654 tied to the mesh at the mesh fold 682 and 684 extends through the lumens of the respective tubes 662 and 664. Moreover, a tension release suture 672 and 674 extending through mesh pores to hold the mesh folds 682 and 684 together extends through the lumens of the respective tubes 662 and 664. The mesh folds 682 and 684 are maintained during implantation by loops 676 and 678 of the respective tension release sutures 672 and 674 passed through the mesh folds 682 and 684. As described above, the suture free ends of tension increase sutures 652 and 654 (or buttons 612 and 614 attached thereto) may be grasped and pulled during the acute post-operative healing phase to directly increase tension of the end portions 42 and 44 and indirectly adjust tension of the central support portion 40. A decrease in sling tension may be obtained by pulling on the exposed free ends of tension decrease sutures 672 and 674 (or buttons 612 and 614 attached thereto) to pull the suture loops 676 and 678 out of the mesh 30 and release the respective folds 682 and 684.

It will be understood that the flexible tubes 662 and 664 may be employed in the embodiments of FIGS. 6-10 to encase the sutures 116 and 118.

Figure 18:
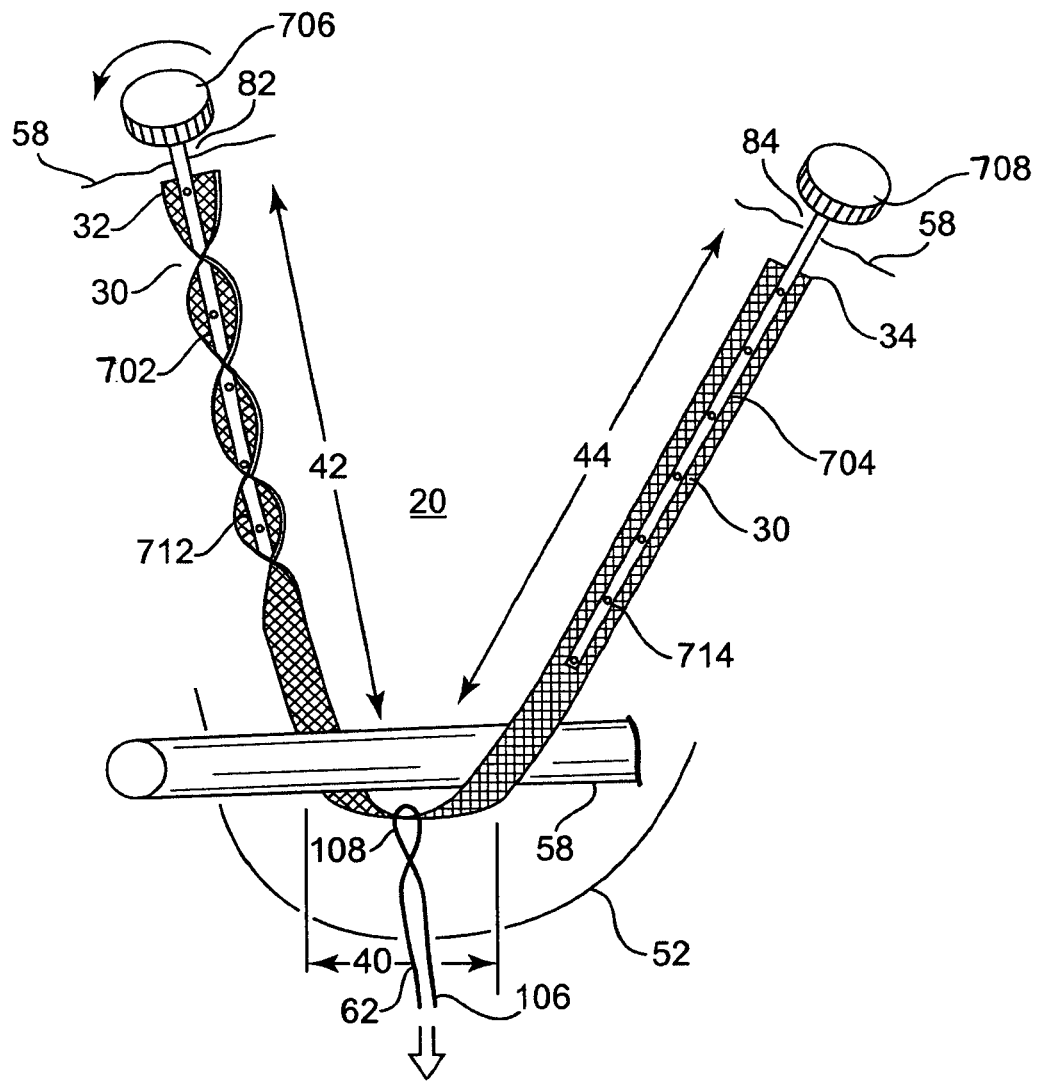
FIG. 18 is a schematic illustration of a further embodiment of an adjustable tension sling of the present invention, wherein tension adjustment bands are extended along sections of the sling end portions and through the skin incisions to external buttons that can be rotated to twist the sling mesh axially to tighten the sling mesh and increase sling tension.

As noted above, the sutures 602, 604 may be twisted to shorten their length and increase sling tension. FIG. 18 illustrates a further embodiment of the a sling of the present invention, wherein the sling mesh 30 is itself twisted to shorten the length of the sling end portions 42 and 44 during the acute post-operative healing phase to directly increase tension of the end portions 42 and 44 and indirectly adjust tension of the central support portion 40. To achieve this twisting it may be necessary to increase torsional rigidity or "twistability" of the sling mesh 30 so that the sling mesh 30 may be twisted about its axis in the sling end portions 42 and 44 to thereby increase tension in the central support portion 40. For example, relatively stiff torque bands 702 and 704 may be extended axially along sections of the sling end portions 42 and 44 and at least periodically affixed to the mesh 30 by thermoplastic rivets 712, 714 or the like. Tensioning devices, e.g., buttons 706 and 708, are provided coupled to the torque bands 702 and 704 extending from the sling free ends 32 and 34 through the respective skin incisions 82 and 84. The sling end portion 42 is twisted by rotation of the button 706 as shown in FIG. 18.

Certain sling implantation procedures for urethral and fecal slings involve employing implantation instruments having needles that are advanced from a first skin incision to a second skin incision to form first and second or right and left tissue pathways around the urethra 58 or the anus 67. The instruments or other instruments are then employed to push or pull the sling end portions 42 and 44 through the first and second pathways to dispose the sling ends near or through the skin incisions 82 and 84 as shown in FIGS. 3 and 4. The above-described embodiments contemplate implantation in such tissue pathways.

Other sling implantation procedures for urethral and fecal slings have sling ends configured to engage sling implantation tool needle ends to be pushed from a single incision adjacent the urethra 58 or the anus 67 through first and second tissue pathways to dispose the sling end portions extending away from the urethra 58 or anus 67. The skin incisions 82 and 84 are not necessarily made, and the sling ends are disposed at subcutaneous locations.

Figure 19:
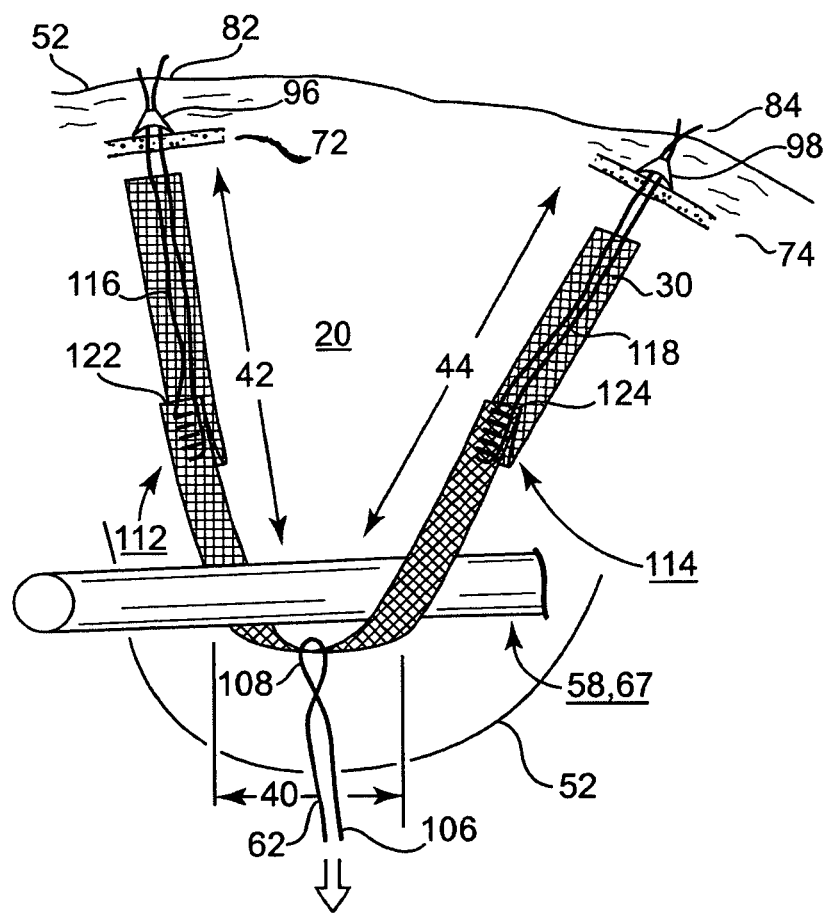
FIG. 19 is a schematic illustration of an adjustable tension sling of FIG. 6 having subcutaneously implanted suture or tissue anchors that can be alternatively coupled to the tension adjustment suture or band free ends in the embodiments of FIGS. 6-18 for subcutaneous implantation abutting tissue layers.

Turning to FIG. 19, it illustrates the adjustable tension sling of FIG. 6 modified with suture or tissue anchors 96 and 98 that can be coupled to the tension adjustment sutures 116 and 118, respectively, for subcutaneous implantation abutting body tissue layers 72 and 74 (e.g., the rectus fascia, the transobturator membrane or other fascia), respectively. Generally speaking, the tissue anchors 96 and 98 can have channels or bores that one or both of the sutures 116 and 118 are passed though that grip the sutures with sufficient force to maintain sling tension. The suture retaining force may be overcome by manipulation of the suture and tissue anchor to increase or decrease sling tension during post-operative recuperation. The suture ends can extend through the skin incisions 82 and 84 and are placed under the skin 52 (or through a vaginal or perineal incision or puncture), and the incisions are then closed. During chronic implantation, adjustments of sling tension may take place by reopening the skin incisions (e.g. 82 and 84) to access the suture ends and the tissue anchors 96 and 98.

In this embodiment, the suture 116 passes through a slidable bore of the tissue anchor 96 and through the same skin incision 82 that the tissue pathway is created for the sling 20. Similarly, the suture 118 is depicted extending through a slidable bore of the tissue anchor 98 and through the same skin incision 84 that the tissue pathway is created for the sling 20. For example, the tissue pathway may extend through the right and left transobturator membranes (tissue layers 72 and 74) that the tissue anchors 96 and 98 are passed through and bear against. In a related embodiment, tissue anchors can be eliminated or substituted with tines on mesh face near the sling ends.

It will be understood that the tissue anchors 96 and 98 and the above-described procedures may be employed in any of the embodiments illustrated in FIGS. 6-12 and 14-17 and variations thereof.

Figure 20:
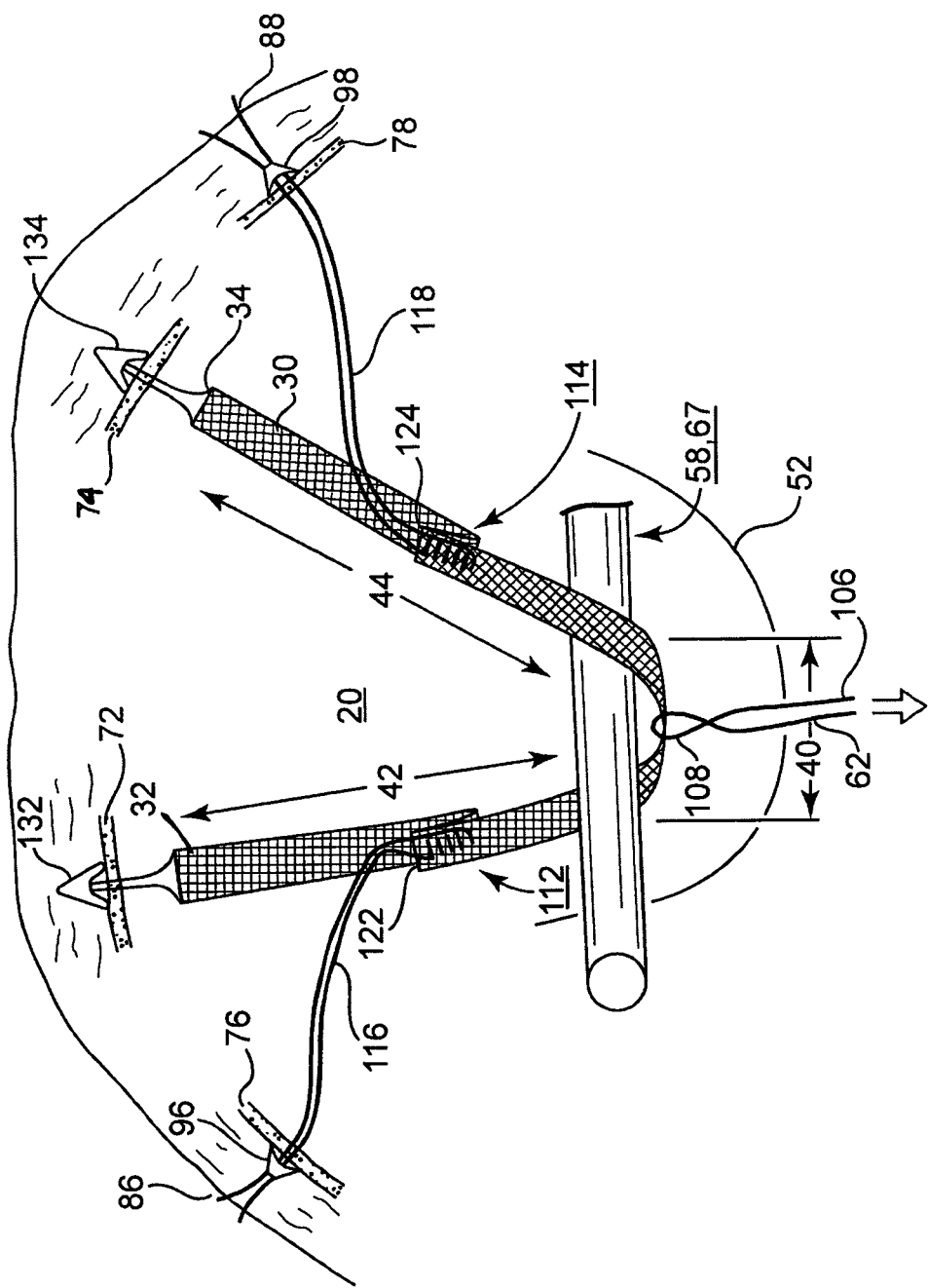
FIG. 20 is a schematic illustration of a further variation of the adjustable tension sling of FIG. 6, wherein the sling ends incorporate tissue anchors passed through and engaging tissue layers, and the tension adjustment sutures extend through or around further tissue anchors and extend through the skin to be available to increase and/or decrease the sling tension.

In a further variation of this embodiment of the invention depicted in FIG. 20, tissue anchors 132 and 134 are coupled to the sling ends 32 and 34, respectively, and the sutures 116 and 118 are passed through the tissue anchors 96 and 98. In the implantation procedure, the tissue anchor 132 and the sling end portion 32 are pushed from a single skin incision below the urethra 58 (or anus 67) through a first tissue pathway such that the tissue anchor 132 is passed through and bears against tissue layer 72. Similarly, the tissue anchor 134 and the sling end portion 34 are pushed from the skin incision below the urethra 58 or anus 67 through a second tissue pathway such that the tissue anchor 134 is passed through and bears against tissue layer 74. In a related embodiment, tissue anchors can be eliminated or substituted with tines on mesh face near the sling ends.

The suture 116 and tissue anchor 96 are pushed through a further tissue pathway such that the tissue anchor 96 is passed through and bears against a separate tissue layer 76 and then through a skin incision 86 (or a perineal or vaginal incision. Similarly, the suture 118 and tissue anchor 98 are pushed through a further tissue pathway such that the tissue anchor 96 is passed through and bears against a separate tissue layer 78 and then through a skin incision 88. Alternatively, the sutures 116 and 118 can first be passed by themselves through the skin incisions 86 and 88, respectively, and the tissue anchors 96 and 98 can be applied over the sutures 116 and 118 to bear against the tissue layers 76 and 78, respectively. In a related embodiment, sutures 116 and 118 can go through a bore in tissue anchors and can be fed down through to vaginal/perineal incision and the fold can be eliminated in this and other embodiments.

Tension can be applied by pulling on the suture ends of sutures 116 and 118, respectively while applying pressure against the subcutaneous tissue anchors 96 and 98, thereby tightening mesh folds 122 and 124. Tension on sutures 116 and 118 can be released to loosen mesh folds 122 and 124 by exposing and manipulating the tissue anchors 96 and 98.

It will be understood that the tissue layers 72, 74, 76, and 78 may comprise a muscle layer, fascia or transobturator membrane. Tissue layers 72 and 76 may be the same or a different tissue layer, and tissue layers 74 and 78 may be the same or a different tissue layer. The particular locations of skin incisions 86 and 88 and the respective tissue anchors 96 and 98 may include transobturator, abdominal, buttocks and perineal.

The tissue anchors 132, 134, 96, and 98 may take any of the forms disclosed in the above-referenced '002 patent and in U.S. Patent Application Publication Nos. 2005/0004576 and 2006/0089525.

Figure 21:
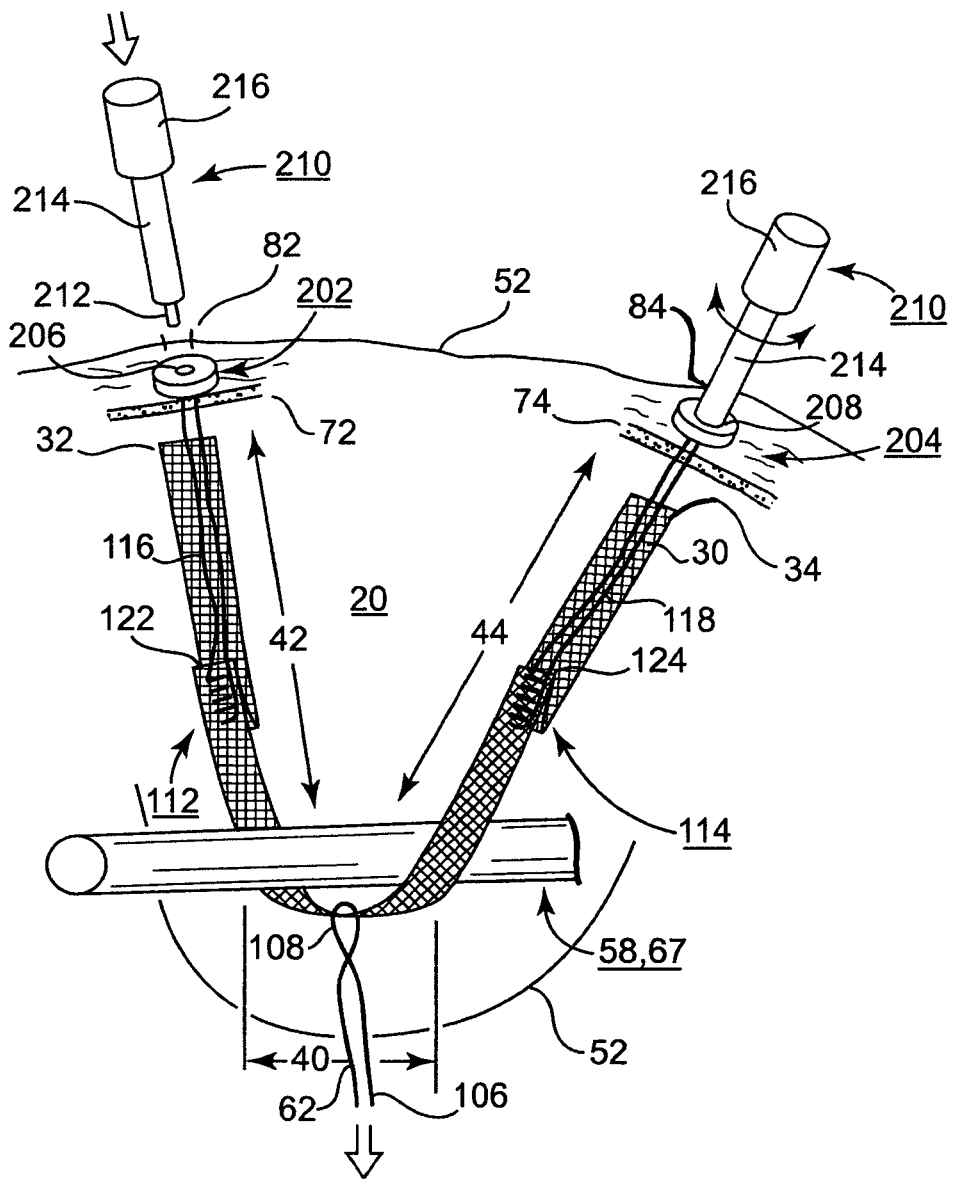
FIG. 21 is a schematic illustration of an adjustable tension sling of FIG. 6 having sling tensioning devices that can be alternatively coupled to the tension adjustment suture or band free ends in the embodiments of FIGS. 6-18 for subcutaneous implantation abutting tissue layers, and an external adjustment actuator is adapted to penetrate the skin and engage the sling tensioning devices.

Turning to FIG. 21, a further modification to the sling 20 of FIG. 6 is illustrated having sling tensioning devices 202 and 204 coupled to and receiving the suture ends of sutures 116 and 118, respectively. The sling tensioning devices 202 and 204 may take the form of those disclosed in the above-referenced '518 and '892 patents. In one approach, the tension adjustment sutures 116 and 118 extend around bobbins within the housings of the sling tensioning devices 202 and 204 that are rotatable in opposite directions to increase or decrease suture tension applied to the mesh folds 122 and 124, respectively. The sling tensioning devices 202 and 204 are implanted subcutaneously bearing against the tissue layers 72 and 74, which may be the same or different tissue layers, depending on the implantation procedure.

The external adjustment actuator 210 may be shaped like a Keith needle having an engaging end 212 at the end of a shaft 214 attached to a handle 216. The tensioning devices 202 and 204 are shaped with actuator end receptacles 206 and 208, respectively, that can be manually palpated through the skin 52. During sling implantation, the actuator engaging end 212 and shaft 214 can be inserted percutaneously through skin incisions 82 and 84 to fit the actuator engaging end 212 into the actuator end receptacles 206 and 208. During chronic implantation, the skin incisions 82 and 84 can be reopened by inserting engaging end 212 through dissection of patient's skin 52 and into the actuator end receptacles 206 and 208, respectively.

The external adjustment actuator 210 is depicted in FIG. 21 poised to be inserted percutaneously through the skin 52 to make engagement with the actuator end receptacle 206 and also depicted in engagement with actuator end receptacle 208. Various rotatable mechanisms within the tensioning devices 202 and 204 are contemplated that can be rotated by manual rotation of the external adjustment actuator 210 in one direction to shorten the sling end portions 42 and 44 together to increase sling tension and that can be rotated by manual rotation of the external adjustment actuator 210 in the other direction to lengthen the sling end portions 42 and 44 to separate apart to decrease sling tension. The actuator engaging end 212 is shaped to both penetrate tissue and to have mating surfaces for engaging the end receptacles 206 and 208 to enable rotation in both directions.

Figure 22:
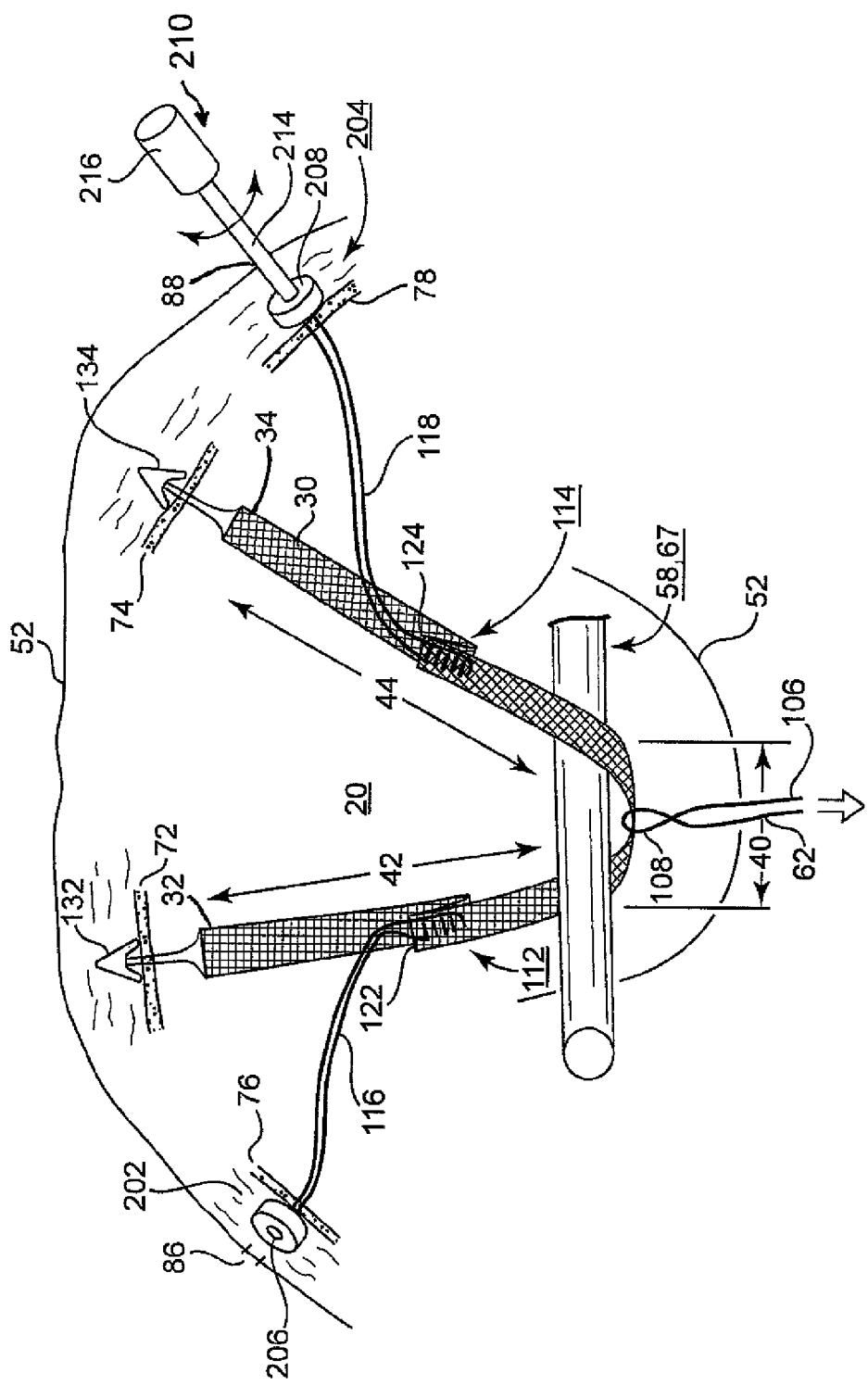
FIG. 22 is a schematic illustration of a further variation of the adjustable tension sling of FIG. 6, wherein the sling ends incorporate tissue anchors passed through and engaging tissue layers, and the tension adjustment sutures extend to sling tensioning devices for subcutaneous implantation abutting tissue layers, and an external adjustment actuator is adapted to penetrate the skin and engage the sling tensioning device.

The embodiment depicted in FIG. 22 is the same as the embodiment depicted in FIG. 20 except for the substitution of the tensioning devices 202 and 204 for the tissue anchors 96 and 98, respectively. Tension is applied to the mesh folds 122 and 124 through adjustment of tensioning devices 202 and 204 using the external adjustment actuator 210 in the same fashion as described above with respect to FIG. 21.

It will be understood that that the sling 20 illustrated in FIGS. 20 and 22 may be modified to eliminate the mesh folds 122 and 124 such that the sutures 116 and 118 may simply be tied (or passed through) to the mesh at the locations of the respective sling adjustment mechanisms 112 and 114. Sling tension would be increased by shortening of the lengths of the sutures 116 and 118 employing either the tissue anchors 96 and 98 of FIG. 20 or the tensioning devices 202 and 204 of FIG. 22.

Moreover, the adjustment sutures 116 and 118 may be extended through sheaths or tubes that may or may not be biodegradable.

Figure 23:
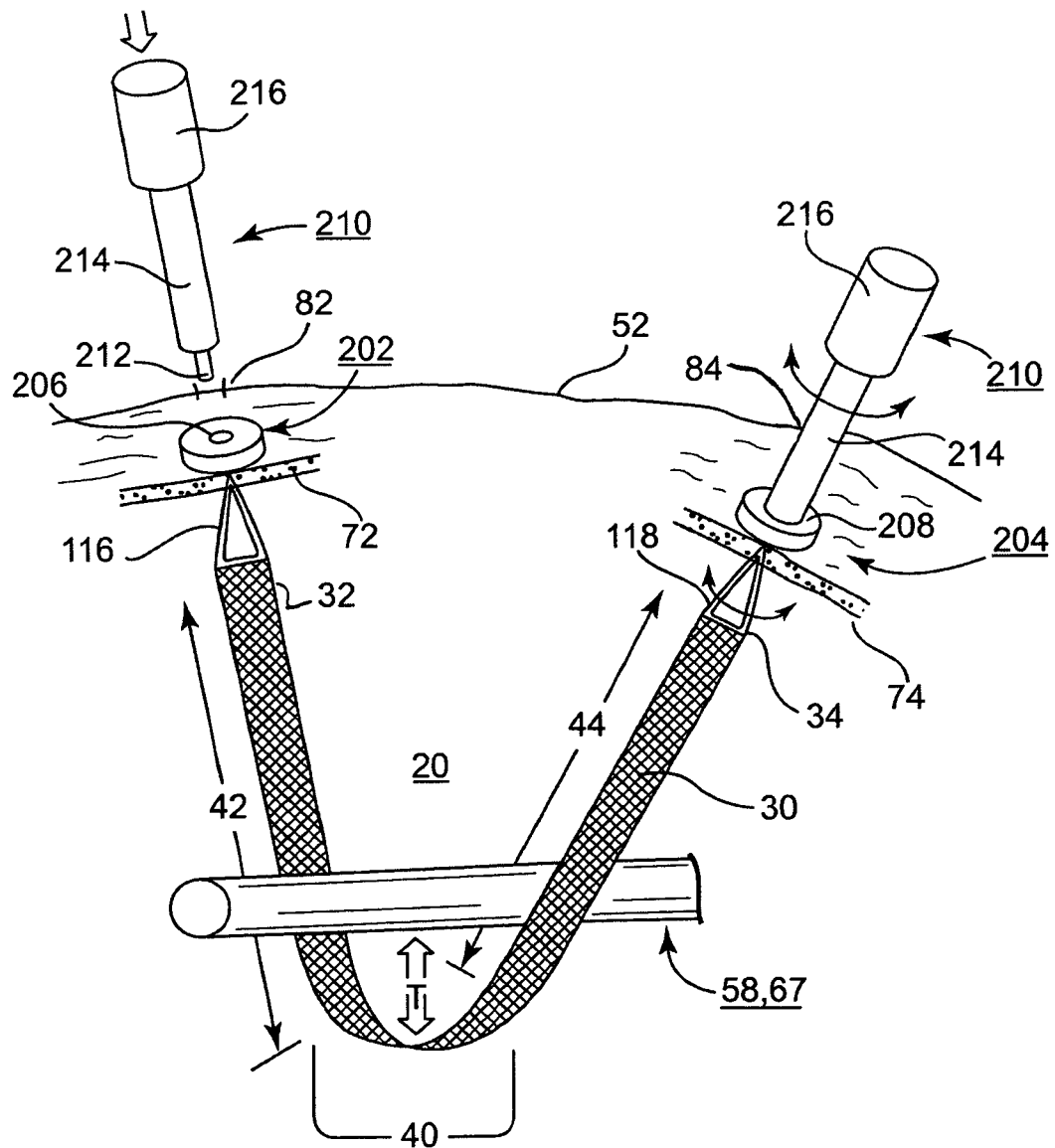
FIG. 23 is a schematic illustration of a further variation of the adjustable tension sling of the present invention, wherein the sling ends are coupled to sutures extending to sling tensioning devices for subcutaneous implantation abutting tissue layers, and an external adjustment actuator is adapted to penetrate the skin and engage the sling tensioning devices.

A simplified embodiment is illustrated in FIG. 23, where the sling 20 is modified to have the sutures 116 and 118 extending from sling ends 32 and 34 to the tensioning devices 202 and 204 implanted to bear against the tissue layers 72 and 74. Again, the external adjustment actuator 210 is depicted in FIG. 21 poised to be inserted percutaneously through the skin 52 to make engagement with the actuator end receptacle 206 and also depicted in engagement with actuator end receptacle 208. Sling tension adjustment is accomplished in the manner described above with respect to FIG. 21.

The lengths of the sling end portions 42 and 44 depicted in FIG. 23 may be considerably shortened or eliminated so that the sling mesh 30 primarily comprises the sling central support portion 40. In that case, the sutures 116 and 118 may be extended through tubes or sheath lumens.

While the above-described embodiments depict methods and apparatus for adjusting sling tension in each sling end portion, in the preferred embodiment one adjustment mechanism may be provided acting on or within one sling end portion.

It will also be understood that the adjustment suture 108 (or other tension adjustment mechanism) acting on the central support portion 40 is depicted in the above-described figures simply as an option and not as a part of the sling end portion tension adjustment mechanisms and techniques.

In the embodiments described above, either one or two sutures or bands extend from each sling end portion 42 and 44. It will be understood that a single suture may be substituted for the pairs of sutures depicted extending from each sling end portion 42 and 44 in certain embodiments.

Figure 24:
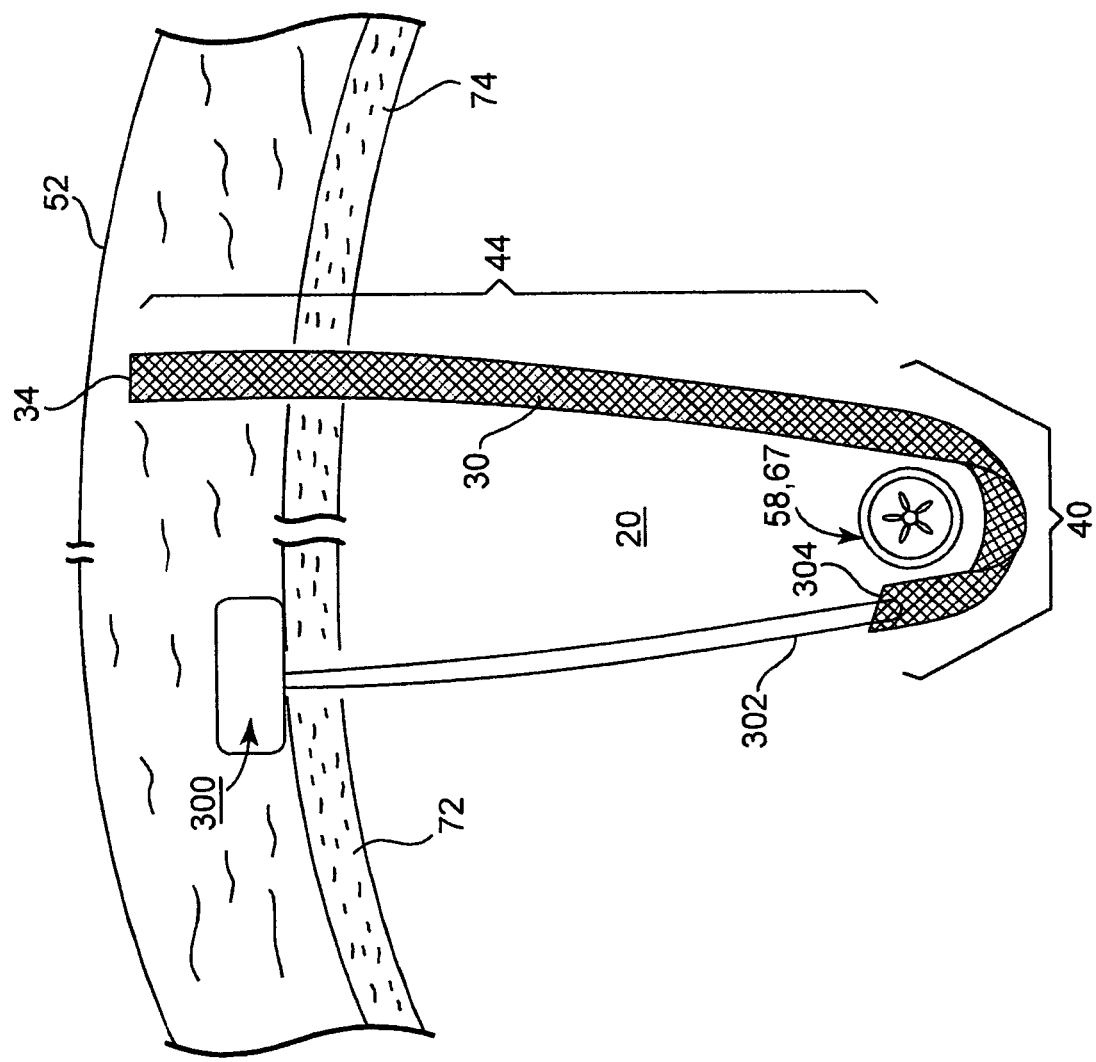
FIG. 24 is a schematic illustration of a further variation of the adjustable tension sling of the present invention, wherein the sling comprises a sling central support portion and one end portion adapted to be extended though a tissue layer and a suture extending from the sling central support portion to a sling tensioning device for subcutaneous implantation abutting a tissue layer using an external adjustment actuator adapted to penetrate the skin to engage the sling tensioning device.

Turning to FIG. 24, it illustrates a further variation of the adjustable tension sling 20 of the present invention, wherein the sling 20 comprises a sling central support portion 40 and one end portion 44 adapted to be extended through a tissue layer 74 and a loop of suture 302 extending from the sling central support portion 40 through a tissue layer 72 to a sling tensioning device 300 adapted to be subcutaneously implanted between the skin 52 and bearing against tissue layer 72. the sling tensioning device 300 may take the form of the sling tensioning devices 202 and 204 and be adjusted using the external adjustment actuator 210 adapted to penetrate the skin 52 in the manner described above with respect to FIG. 21. It will also be understood that a tissue anchor, e.g., tissue anchor 134 may be provided in a related embodiment at sling end 34 to bear against tissue layer 74 as depicted in FIG. 22.

FIG. 25 is a schematic illustration of a further variation of the adjustable tension sling 20 of the present invention, wherein sutures 312 and 314 extend through the sling end portions 42 and 44, respectively to be extended though a tissue layer 72 or 74 to a sling tensioning device 310 adapted to be subcutaneously implanted below the skin 52 and abutting the tissue layer 72 or 74. The sling tensioning device 310 may take the form of the sling tensioning devices 202 and 204 and be adjusted using the external adjustment actuator 210 adapted to penetrate the skin 52 in the manner described above with respect to FIG. 21. In the implantation of the sling 20 depicted in FIG. 24, the tissue layer 72 or 74 may comprise the rectus fascia. The embodiments depicted in FIGS. 24 and 25 provide for post-operative adjustment of the sling device; from hours to months after implantation.

It will be understood that the single tensioning device 310 may be substituted for the two separate sling tensioning devices 202 and 204 depicted in FIGS. 21 and 23. In these variations of sling 20 illustrated in FIGS. 21 and 23, the sutures 116 and 118 would extend to the single sling tensioning device 310.

Many of the embodiments described herein can be used in connection with prolapse and pelvic floor repairs (men and women) that may require post-operative adjustment of the implanted mesh or graft or sling. They may also be used in connection with prostatectomies or hysterectomies and to support any other body tissue within the pelvic area or other parts of the body including but not limited to, hernia repair, and shoulder and abdominal repairs. Examples of meshes, grafts and prolapse repairs are described in U.S. Publication Nos. 2004-0039453 A1, 2005-0250977 A1, and 2005-0245787 A1, which are hereby incorporated by reference in their entirety.

All patents and publications referenced herein are hereby incorporated, by reference in their entireties.

The invention claimed is:

1. A system for providing support to body tissue to alleviate incontinence, the system comprising:
   an elongated incontinence sling comprising:
      first and second longitudinal edges;
      a central support portion positionable to support the urethra or anus and comprising a first end and a second end;
      a first sling end portion extending from the first end of the central support portion, the first sling end portion comprising a first sling end extending between the first and second longitudinal edges and spaced from the central support portion;
      a second sling end portion extending from the second end of the central support portion, the second sling end portion comprising a second sling end extending between the first and second longitudinal edges and spaced from the central support portion;
   at least one tension adjustment suture coupled to at least a portion of a length of the first sling end portion, the tension adjustment suture extending between a proximal location along a length of the first sling end portion to a distal location along a length of the first sling end portion, the distal location being located distal to the proximal location, wherein the tension adjustment suture includes a suture free end extending from the first sling end portion at the distal location, wherein the tension adjustment suture does not extend into the central support portion; and
   a tensioner coupled to the suture free end, wherein the tensioner is manipulatable to release or apply tension through the first sling end portion to the central support portion.

2. The system of claim 1, wherein the first and second sling end portions comprise a plurality of mesh pores, and wherein the tension adjustment suture is looped through the mesh pores to form a fold within the first sling end portion that may be tightened or loosened by application or release of tension through the suture.

3. The system of claim 1, further comprising:
   at least one elongated tube having a tube lumen extending between tube first and second ends, wherein the at least one tension adjustment suture extends through the tube lumen.

4. The system of claim 1, further comprising:
   at least one elongated sheath having a sheath lumen extending between sheath first and second ends, wherein the at least one tension adjustment suture and at least one of the sling end portions extend through the sheath lumen.

5. The system of claim 4, wherein each elongated sheath has an exterior sheath surface configured or treated to increase frictional engagement with surrounding tissue.

6. The system of claim 1, wherein the tensioner is coupled to the suture free end for rotating the free end to release or apply tension through the first or second sling end portion to the central support portion.

7. The system of claim 1, wherein the tensioner is subcutaneously implantable to bear against a tissue layer and comprises tension adjustment means coupled to the suture free end for drawing the tension adjustment suture toward the tissue layer to apply tension through the first sling end portion to the central support portion.

8. The system of claim 7, further comprising:
an external adjustment instrument having a shaft extending between a handle and an engaging end shaped to be percutaneously advanced through the skin; wherein the tensioner is engageable by the engaging end of the external adjustment instrument for operating the tension adjustment means to increase or decrease the tension.

9. The system of claim 7, further comprising at least one tissue anchor coupled to the first sling end capable of being passed through body tissue to anchor the first sling end against a tissue layer to stabilize the first sling end and facilitate adjustment of sling tension.

10. The system of claim 1, wherein the tensioner is coupled to the suture free end and is capable of axially pulling the tension adjustment suture to release or apply tension through the first sling end portion to the central support portion.

11. The system of claim 10, wherein the tensioner is subcutaneously implantable to bear against a tissue layer.

12. The system of claim 11, further comprising at least one tissue anchor coupled to the first sling end and capable of being passed through body tissue to anchor first sling end against a tissue layer to stabilize the first sling end and facilitate adjustment of sling tension.

13. The system of claim 1, further comprising at least one tissue anchor coupled to the first sling end and capable of being passed through body tissue to anchor at the first sling end against a tissue layer to stabilize the first sling end and facilitate adjustment of sling tension.

14. The system of claim 1, further comprising a tissue anchor having a bore that receives tension adjustment suture, wherein the tissue anchor is manipulatable to anchor against a tissue layer and to maintain tension in the central support portion applied to the urethra or anus.

15. The system of claim 1, comprising
a second tension adjustment suture coupled to at least a portion of a length of the second sling end portion, the second tension adjustment suture extending between a proximal location along a length of the second sling end portion to a distal location along a length of the second sling end portion, the distal location being distal to the proximal location, wherein the second tension adjustment suture includes a second suture free end extending from the second end portion at the distal location, wherein the second tension adjustment suture does not extend into the central support portion; and;
a second tensioner subcutaneously implantable to bear against a tissue layer and coupled to the second suture free end and capable of drawing the second tension adjustment suture toward the tissue layer to apply tension through the second sling end portion to the central support portion.

16. The system of claim 15, further comprising:
a second elongated external adjustment instrument having a shaft extending between a handle and an engaging end shaped to be percutaneously advanced through the skin; wherein the second tensioner is engageable by the engaging end of the second external adjustment instrument for operating the second tensioner to increase or decrease sling tension.

17. The system of claim 1, further comprising an adjustment suture coupled to the central support portion, wherein the adjustment suture is capable of manual tension adjustment.

18. The system of claim 1, wherein the tensioner comprises a housing and a bobbin, wherein the housing receives the tension adjustment suture and the tension adjustment suture is rotatable around the bobbin to increase or decrease sling tension.

19. The system of claim 1, wherein the at least one tension adjustment suture comprises two suture free ends.

20. The system of claim 1, wherein the tensioner is capable of releasing or applying tension through the first sling end portion to the central support portion by increasing or decreasing a length of the first sling end portion.

* * * * *

UNITED STATES PATENT AND TRADEMARK OFFICE
CERTIFICATE OF CORRECTION

Page 1 of 2

PATENT NO.       : 8,628,463 B2
APPLICATION NO.  : 12/308598
DATED            : January 14, 2014
INVENTOR(S)      : Ogdahl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1177 days.

Title Page, Item (56), under "OTHER PUBLICATIONS", Column 2, Lines 1-3, delete ""Introducing: AlloSling Fascia The Natural Choice for Suburethral Sling Provedures", Advertisement from UroMed Corporation (1 page).".

On Title Page 4, Item (56), under "OTHER PUBLICATIONS", Column 1, Line 6, delete "AlloSource product literature (11 pages)."

On Title Page 4, Item (56), under "OTHER PUBLICATIONS", Column 2, Line 43, delete "et al," and insert -- et al., --, therefor at each occurrence throughout the Other Publications; Column 2, Line 47, delete "Incontintence," and insert -- Incontinence, --, therefor; Column 2, Line 52, delete "Incontience," and insert -- Incontinence, --, therefor.

On Title Page 5, Item (56), under "OTHER PUBLICATIONS", Column 1, Line 6, delete "Advaned" and insert -- Advanced --, therefor; Column 1, Line 28, delete "Springer-Veglag," and insert -- Springer Verlag, --, therefor.

On Title Page 5, Item (56), under "OTHER PUBLICATIONS", Column 2, Line 17, delete "Suspenison," and insert -- Suspension, --, therefor.

Signed and Sealed this
Sixth Day of January, 2015

Michelle K. Lee
*Deputy Director of the United States Patent and Trademark Office*

CERTIFICATE OF CORRECTION (continued)
U.S. Pat. No. 8,628,463 B2

In the Specification

Column 2, Line 27, delete "uethra" and insert -- urethra --, therefor; Column 2, Line 30, delete "patents:" and insert -- patents. --, therefor.

Column 7, Line 11, delete "stabilze" and insert -- stabilize --, therefor.

Column 8, Line 23, delete "proplapse" and insert -- prolapse --, therefor.

Column 9, Line 37, delete "proplapse" and insert -- prolapse --, therefor.

Column 17, Line 37, delete "72. the" and insert -- 72. The --, therefor.

In the Claims

Column 19, Line 16, in Claim 8, delete "the tension" and insert -- each tension --, therefor; Column 19, Line 31, in Claim 12, delete "anchor first" and insert -- anchor the first --, therefor.

Column 19, Line 40, in Claim 14, delete "receives tension" and insert -- receives the tension --, therefor.

Column 20, Line 1, in Claim 15, delete "comprising" and insert -- comprising: --, therefor; Column 20, Line 12, in Claim 15, delete "portion; and;" and insert -- portion; --, therefor.